United States Patent
Kolopp-Sarda et al.

(10) Patent No.: US 8,021,836 B2
(45) Date of Patent: Sep. 20, 2011

(54) METHOD OF DIAGNOSING INFECTIOUS DISEASE BY MEASURING THE LEVEL OF SOLUBLE TREM-1 IN A SAMPLE

(75) Inventors: Marie Nathalie Kolopp-Sarda, Vandoeuvre les Nancy (FR); Marie-Christine Bene, Vandoeuvre les Nancy (FR); Paola Panina, Milan (IT); Pietro Di Lucia, Milan (IT); Bruno Levy, Nancy Cédex (FR); Pierre-Edouard Bollaert, Nancy Cédex (FR); Gilbert Faure, Vandoeuvre les Nancy (FR); Sebastien Gibot, Vandoeuvre les Nancy (FR)

(73) Assignee: Université Henri Poincaré-Nancy I, Cedex, Nancy (FR)

( * ) Notice: Subject to any disclaimer, the term of this patent is extended or adjusted under 35 U.S.C. 154(b) by 650 days.

(21) Appl. No.: 10/587,356

(22) PCT Filed: Jan. 27, 2005

(86) PCT No.: PCT/GB2005/000273
§ 371 (c)(1), (2), (4) Date: Jun. 25, 2007

(87) PCT Pub. No.: WO2005/071408
PCT Pub. Date: Aug. 4, 2005

(65) Prior Publication Data
US 2007/0281319 A1 Dec. 6, 2007

(30) Foreign Application Priority Data
Jan. 27, 2004 (GB) .................................. 0401730.7

(51) Int. Cl.
*C12Q 1/68* (2006.01)
(52) U.S. Cl. ........................................................ 435/6
(58) Field of Classification Search ........................ None
See application file for complete search history.

(56) References Cited

U.S. PATENT DOCUMENTS 6,420,526 B1 7/2002 Ruben et al.
2003/0165875 A1* 9/2003 Colonna et al. ................... 435/6

FOREIGN PATENT DOCUMENTS

WO WO 02/058721 A 8/2002
WO WO 2004/035732 A 4/2004
WO WO 2004/081233 A 9/2004

OTHER PUBLICATIONS

Bouchon et al., "Cutting edge: inflammatory responses can be triggered by TREM-1, a novel receptor expressed on neutrophils and monocytes," *Journal of Immunology*, vol. 164, 2000, pp. 4991-4995.
Nathan et al., "TREM-1: a new regulator of innate immunity in sepsis syndrome," *Nature Medicine*, vol. 7, No. 5, 2001, pp. 530-532.
Bouchon et al., "TREM-1 amplifies inflammation and is a crucial mediator of septic shock," *Nature*, vol. 410, No. 6832, Apr. 26, 2001, pp. 1103-1107.
Colonna et al., "TREM-1 (triggering receptor expressed on myeloid cells): a new player in acute inflammatory responses," *Journal of Infectious Diseases*, vol. 187, No. SUPPL 2, Jun. 15, 2003, pp. S397-S401.
Nochi et al., "Modulation of hepatic granulomatous responses by transgene expression of DAP12 or TREM-1-Ig molecules," *American Journal of Pathology*, vol. 162, No. 4, Apr. 2003, pp. 1191-1201.
Gingras et al., "TREM-1 MDL-1, and DAP12 expression is associated with a mature stage of myeloid development," *Molecular Immunology*, vol. 38, No. 11, Mar. 2002, pp. 817-824.

* cited by examiner

*Primary Examiner* — Gary B. Nickol
*Assistant Examiner* — Khatol Shahnan-Shah
(74) *Attorney, Agent, or Firm* — Foley & Lardner LLP

(57) ABSTRACT

The present invention concerns a method of diagnosing disease of bacterial or fungal origin in a subject, which method comprises the step of measuring the level of Strem-1 in a biological sample obtained from said subject.

11 Claims, 11 Drawing Sheets

```
ctactactac taaattcgcg gccggtcgac gctggtgcac aggaaggatg aggaagacca    60
ggctctgggg gctgctgtgg atgctctttg tctcagaact ccgagctgca actaaattaa   120
ctgaggaaaa gtatgaactg aaagaggggc agaccctgga tgtgaaatgt gactacacgc   180
tagagaagtt tgccagcagc cagaaagctt ggcagataat aagggacgga gagatgccca   240
agaccctggc atgcacagag aggccttcaa agaattccca tccagtccaa gtggggagga   300
tcatactaga agactaccat gatcatggtt tactgcgcgt ccgaatggtc aaccttcaag   360
tggaagattc tggactgtat cagtgtgtga tctaccagcc tcccaaggag cctcacatgc   420
tgttcgatcg catccgcttg gtggtgacca agggttttc agggacccct ggctccaatg    480
agaattctac ccagaatgtg tataagattc ctcctaccac cactaaggcc ttgtgcccac   540
tctataccag ccccagaact gtgacccaag ctccacccaa gtcaactgcc gatgtctcca   600
ctcctgactc tgaaatcaac cttacaaatg tgacagatat catcagggtt ccggtgttca   660
acattgtcat tctcctggct ggtggattcc tgagtaagag cctggtcttc tctgtcctgt   720
ttgctgtcac gctgaggtca tttgtaccct aggcccacga acccacgaga atgtcctctg   780
acttccagcc acatccatct ggcagttgtg ccaagggagg agggaggagg taaaaggcag   840
ggagttaata acatgaatta aatctgtaat caccagctat ttct                    884
```

[SEQ ID No: 1]

Fig. 1

```
Met Arg Lys Thr Arg Leu Trp Gly Leu Leu Trp Met Leu Phe Val Ser
1               5                   10                  15
Glu Leu Arg Ala Ala Thr Lys Leu Thr Glu Glu Lys Tyr Glu Leu Lys
            20                  25                  30
Glu Gly Gln Thr Leu Asp Val Lys Cys Asp Tyr Thr Leu Glu Lys Phe
            35                  40                  45
Ala Ser Ser Gln Lys Ala Trp Gln Ile Ile Arg Asp Gly Glu Met Pro
    50                  55                  60
Lys Thr Leu Ala Cys Thr Glu Arg Pro Ser Lys Asn Ser His Pro Val
65              70                  75                      80
Gln Val Gly Arg Ile Ile Leu Glu Asp Tyr His Asp His Gly Leu Leu
                85                  90                  95
Arg Val Arg Met Val Asn Leu Gln Val Glu Asp Ser Gly Leu Tyr Gln
                100                 105                 110
Cys Val Ile Tyr Gln Pro Pro Lys Glu Pro His Met Leu Phe Asp Arg
            115                 120                 125
Ile Arg Leu Val Val Thr Lys Gly Phe Ser Gly Thr Pro Gly Ser Asn
    130                 135                 140
Glu Asn Ser Thr Gln Asn Val Tyr Lys Ile Pro Pro Thr Thr Thr Lys
145                 150                 155                 160
Ala Leu Cys Pro Leu Tyr Thr Ser Pro Arg Thr Val Thr Gln Ala Pro
            165                 170                 175
Pro Lys Ser Thr Ala Asp Val Ser Thr Pro Asp Ser Glu Ile Asn Leu
            180                 185                 190
Thr Asn Val Thr Asp Ile Ile Arg Val Pro Val Phe Asn Ile Val Ile
        195                 200                 205
Leu Leu Ala Gly Gly Phe Leu Ser Lys Ser Leu Val Phe Ser Val Leu
    210                 215                 220
Phe Ala Val Thr Leu Arg Ser Phe Val Pro
225                 230
```

[SEQ ID No: 2]

Fig. 2

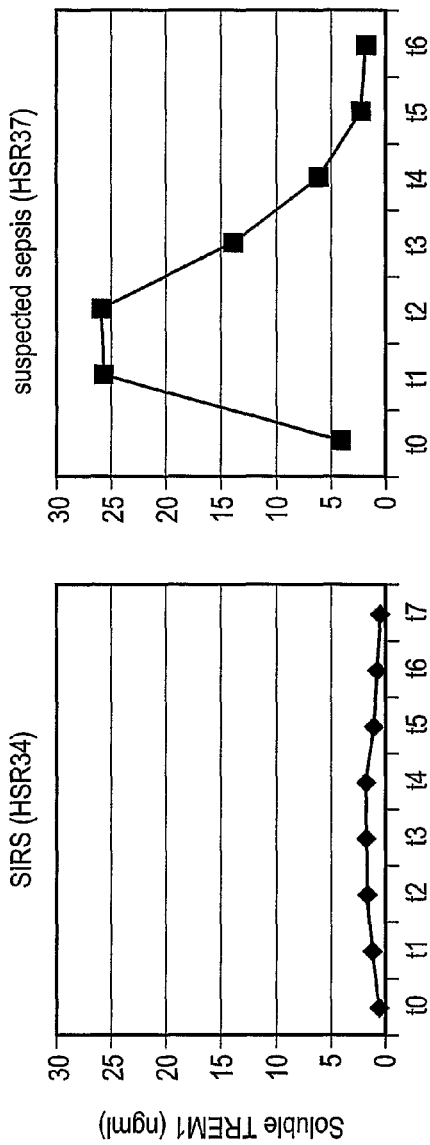
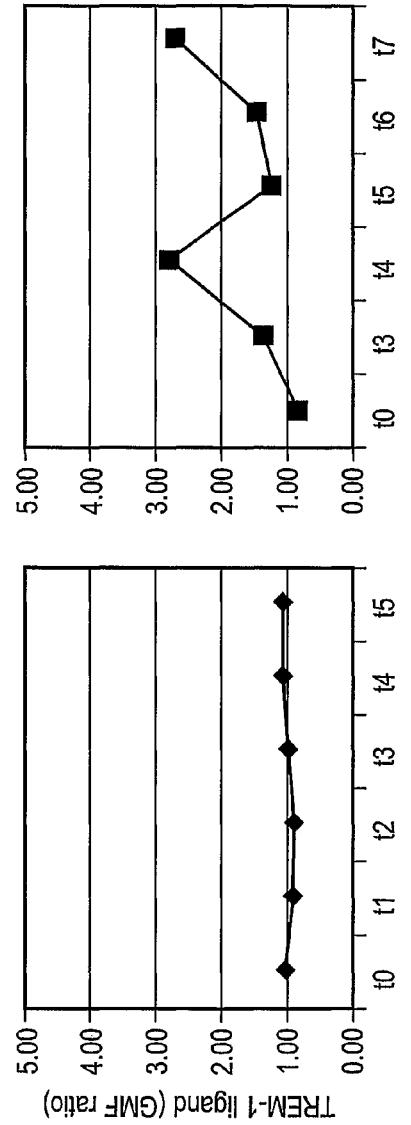
Fig. 11A
Fig. 11B

METHOD OF DIAGNOSING INFECTIOUS DISEASE BY MEASURING THE LEVEL OF SOLUBLE TREM-1 IN A SAMPLE

This invention relates generally to the field of immunology. More particularly, the present invention relates to inflammation and the use of markers that allow the prompt diagnosis of infectious disease (for example of bacterial or fungal) origin and the follow up of infected patients during pharmacological treatment. These markers have particular applications in the diagnosis of pneumonia and sepsis.

SEQUENCE LISTING

The instant application contains a Sequence Listing which has been submitted via EFS-Web and is hereby incorporated by reference in its entirety. Said ASCII copy, created on Mar. 23, 2010, is named 59718108.txt and is 4,298 bytes in size.

The diagnosis and treatment of infectious pneumonia in ventilated patients remain a challenge for clinicians. A presumptive clinical diagnosis of pneumonia is often made when a patient develops a new radiographic infiltrate associated with fever, leukocytosis and purulent tracheal secretions and when micro-organisms are isolated from the airways. Unfortunately, many non-infectious processes may be responsible for fever and new pulmonary infiltrates in mechanically ventilated patients and then, clinical approaches lead to an overestimation of the incidence of pneumonia. Moreover, whatever the microbiological diagnostic procedure chosen, it requires further laboratory processing with unavoidable delays of 24 to 48 hours before obtaining definitive quantitative microbial culture results. Meanwhile, clinicians often feel uncomfortable about the diagnosis and, in many cases, unneeded antibiotics are administered while waiting for laboratory results. Therefore, many biological markers have previously been studied to improve the rapidity and performance of the diagnosis procedure but with disappointing results.

In the Examples herein the Inventors describe a rapid detection test of the soluble form of the human TREM-1 receptor (sTREM-1) in bronchoalveolar fluid of mechanically ventilated patients to accurately diagnose bacterial or fungal pneumonia.

Many non-infectious processes lead to fever and new pulmonary infiltrates in the mechanically ventilated patient, rendering the diagnosis of pneumonia (and especially ventilator-associated pneumonia) very challenging. The systemic signs of infection, such as fever, tachycardia, and leukocytosis, are non-specific findings and can be caused by any condition that releases cytokines. Pugin et al. (Am Rev Respir Dis 1991; 143:1121-9) combined body temperature, white blood cells count, volume and appearance of tracheal secretions, ratio of the partial pressure of arterial oxygen to the fraction of inspired oxygen (PaO2/FiO2), chest-X-ray, and tracheal aspirate cultures into a clinical pulmonary infection score (CPIS) and reported that a score >6 was associated with a high likelihood of pneumonia. This was confirmed in the Inventors' study since a clinical pulmonary infection score >6 was the best clinical predictor of pneumonia with an odds ratio of 2.98. However, the diagnostic accuracy of this score remains to be confirmed.

In terms of clinical decision-making in patients in whom pneumonia is suspected, the major problem with the microbiological diagnostic procedure chosen, which is still matter of debate, is that it requires samples cultures, which implies waiting for at least 24 to 48 hrs after sampling. During this delay, the uncertainty of the clinician towards the patient's diagnosis often leads to the prescription of unneeded antibiotics. However, the use of empirical broad-spectrum antibiotics in patients without infection is potentially harmful, facilitating colonization and superinfection with multiresistant bacteria and has been shown to be correlated with an increased length of hospital stay and therefore increased hospital costs. In addition, antibiotic overuse in such critically ill patients delays the proper diagnosis and treatment of the true cause of fever and pulmonary infiltrate.

Many biological markers have been studied in the hope to improve the rapidity and performance of the diagnosis procedure. Among them, serum C reactive protein and procalcitonin have been disappointing in critically ill patients. Similar results have been obtained in the Inventors' studies with no significant differences between pulmonary infected patients and non-infected patients.

When anatomical and mechanical defence mechanisms preventing micro-organisms from reaching alveoli are overwhelmed, a complex host response develops. This response comprises the activation, by microbial products, of alveolar macrophages which locally release multiple endogenous mediators. Among these mediators, tumor necrosis factor-α (TNFα), interleukin-1β (IL-1β) and other cytokines have been demonstrated to be increased in various types of pulmonary infectious challenges with potential prognostic implications. However, in agreement with other studies, (for example see Monton C et al. Crit Care Med 1999; 9:1745-53). the Inventors were unable to determine accurate discriminating cut-off level of such mediators for the diagnosis of pneumonia.

The Inventors, using an easy-to-perform immunoblot technique, demonstrate herein that a soluble form of TREM-1 (sTREM-1) is released locally in the bronchoalveolar lavage fluid from patients suffering from pneumonia with a sensitivity of at least 98 percent. In striking contrast, sTREM-1 was detected in only 6 out of 64 patients without pneumonia. Bronchoalveolar lavage fluid levels of sTREM-1 were not correlated to any of the clinical or biological parameters tested and stood as an independent parameter of high specificity. In a multiple logistic regression analysis, presence of sTREM-1 in bronchoalveolar lavage fluid was shown to be the best predictor of pneumonia with an odds ratio as high as 41.52. Presence of sTREM-1 by itself was more accurate that any clinical findings or laboratory values in identifying the existence of bacterial or fungal pneumonia. Thus rapid detection of sTREM-1 in bronchoalveolar lavage fluid is useful in establishing or excluding the diagnosis of bacterial or fungal pneumonia.

Sepsis is a common cause of morbidity and mortality in intensive care units (ICUs). Clinical and laboratory signs of systemic inflammation including changes in body temperature, tachycardia or leukocytosis are neither sensitive nor specific enough for the diagnosis of sepsis and can be misleading because critically ill patients often present a systemic inflammatory response syndrome (SIRS) without infection. This issue is of paramount importance owing to the fact that therapy and outcome differ greatly between patients with and those without sepsis. Moreover, the widespread use of antibiotics for all such patients is likely to increase antibiotic resistance, toxicity and costs. Thus, there is a so far unsatisfied need for clinical or laboratory tools allowing to distinguish between SIRS and sepsis. Among the potentially useful markers of sepsis, procalcitonin (PCT) has been suggested to be the most promising one. Procalcitonin levels have been postulated to be superior to clinical variables or commonly used laboratory tests, such as C-reactive protein (CRP) levels or leukocyte count, and even to correlate with the severity of microbial invasion. However, several investigators have questioned the diagnostic and prognostic accuracy of routine POT measurements, reporting inconsistent and variable results depending on the severity of illness and infection in the patient population studied. Sepsis constitutes a significant consumption of intensive care resources and remains an ever-present problem in the intensive care unit. It has been estimated that between 400 000 and 500 000 patients are so affected each year in both the USA and Europe. Morbidity and mortality have remained high despite improvements in both supportive and anti-microbial therapies. Mortality rates vary from 40% for uncomplicated sepsis to 80% in those suffering from septic shock and multi-organ dysfunction. The pathogenesis of the conditions is now becoming better understood. Greater understanding of the complex network of immune, inflammatory and haematological mediators may allow the development of rational and novel therapies.

The condition of sepsis has previously been associated with many terms and nomenclature, reflecting both the complexity of the condition and the similarity of the inflammatory response secondary to other aetiologies. To illustrate the complex nature of sepsis, sepsis has been defined by Edward O. Uthman, MD, as "a constellation of clinical and laboratory findings from which an experienced physician concludes that the patient may have a serious infection". His definition was purposely made as a nebulous, subjective, and tautological definition, because attempts to define "sepsis" in the literature have stirred a great deal of disagreement and qualification.

In 1991, the American College of Chest Physicians and the American Society of Critical Care Medicine published definitions for systemic inflammatory response syndrome (SIRS) and sepsis, with the aim of clarifying the diagnosis and treatment of these conditions and to aid interpretation of research in this field (see Table 1).

TABLE 1

Definitions for the systemic inflammatory response syndrome (SIRS) and sepsis

| SIRS Two or more of: | 1. Temperature > 38° C. or > 36° C.<br>2. Tachycardia > 90 beats/minute<br>3. Respiratory rate > 20 breaths/minute or $PaCO_2$ < 4.3 kPa<br>4. White blood count > 12 × $10^9$/l or < 4 × $10^9$/l or > 10% immature (band) forms |
|---|---|
| Sepsis: | SIRS clue to infection |
| Severe sepsis: | Sepsis with evidence of organ hypoperfusion |
| Septic shock: | Severe sepsis with hypotension (systolic BP < 90 mmHg) despite adequate fluid resuscitation or the requirement for vasopressors/inotropes to maintain blood pressure |

A pattern of physiological variables have been shown in critically ill patients in response to a range of insults including; trauma, burns, pancreatitis and infection. These include inflammatory responses, leucocytosis or severe leucopaenia, hyperthermia or hypothermia, tachycardia and tachypnoea and have been collectively termed the systemic inflammatory response syndrome (SIRS). This definition emphasises the importance of the inflammatory process in these conditions regardless of the presence of infection. The term sepsis is reserved for SIRS when infection is suspected or proven.

Sepsis is further stratified into severe sepsis when there is evidence of organ hypoperfusion, made evident by signs of organ dysfunction such as hypoxaemia, oliguria, lactic acidosis or altered cerebral function. Septic shock is severe sepsis complicated by hypotension defined as systolic blood pressure less than 90 mmHg despite adequate fluid resuscitation. Sepsis and SIRS may be complicated by the failure of two or more organs, termed multiple organ failure (MOF), due to disordered organ perfusion and oxygenation. In addition to systemic effects of infection, a systemic inflammatory response may occur in severe inflammatory conditions such as pancreatitis and burns.

The appearance of signs of an inflammatory response is less well defined following traumatic insults. In the intensive care unit, gram-negative bacteria are implicated in 50 to 60% of sepsis with gram-positive bacteria accounting for a further 35 to 40% of cases. The remainder of cases are due to the less common causes of fungi, viruses and protozoa.

Early recognition of sepsis and Systemic Inflammatory Response Syndrome (SIRS) in the critically ill patient may avoid the increased morbidity, mortality and length of stay associated with multiple organ failure. However, there are major problems associated with diagnosis of sepsis and a clear need exists for rapid, reliable and sensitive methods to detect, monitor and treat SIRS due to infectious agents (sepsis).

The present invention is directed towards circumventing the existing problems associated with diagnosing sepsis to provide an accurate and consistent method of detection. In the Examples herein the Inventors describe the value of assaying the soluble form of TREM-1 (sTREM-1) in plasma samples of newly admitted critically ill patients with suspected sepsis as a new approach to accurately diagnose infectious processes.

Early identification of infection has a major impact on the clinical course, management and outcome of critical patients. Critical care physicians have at their disposal a variety of indicators to serve as a guide in discriminating infectious from non-infectious conditions in newly admitted patients. In some cases, the diagnosis of sepsis becomes clear after completing the medical history and physical examination of a newly admitted patient (Bates D W, et al. Ann Intern Med. 1990; 113:495-500). In other circumstances of non-infectious insults causing SIRS (e.g., trauma, haemorrhage, burn, pancreatitis, etc.), the diagnosis of sepsis remains challenging. Efforts have thus been made to identify a reliable marker of infection. However, to date, no single clinical or biological indicator of sepsis has gained widespread acceptance. Among the potentially useful sepsis markers, procalcitonin has been proposed to be the most promising one, but this has been challenged by several authors.

In the study described in Example 3 herein, plasmatic sTREM-1 level appears to be the best independent predictor of sepsis. At a cut-off level of 600 ng/mL, the positive and negative predictive values are 94 and 92% respectively. This study has an important implication for clinicians. As a putative new test to diagnose sepsis upon ICU admission, plasmatic sTREM-1 level assay offers a higher degree of certainty than other currently available candidates. This accuracy can usefully guide physicians in their clinical decision-making and stepwise approach to the complex management of critically ill patients. The immunoblot technique used here can be performed within 3 to 4 hours and may provide valuable information long before blood culture results are back. Moreover, it is of low cost and can be applied to small series or even individual samples.

The results reported here demonstrate that rapid measurement of the plasmatic sTREM-1 levels may improve the ability of clinicians to differentiate patients with sepsis from those with systemic inflammation of non-infectious origin. This should be especially useful among patients in whom the diagnosis is not clinically straightforward. The immunoblot technique described is rapid, accurate, of low cost and can be applied to small series or even individual samples. Use of this test to assess plasmatic sTREM-1 levels should lead to a more accurate diagnosis of sepsis in patients admitted in ICUs with a clinical suspicion of infection.

The triggering receptor expressed on myeloid cells-1 (TREM-1) is a member of the Ig-superfamily, the expression of which is up-regulated on phagocytic cells in the presence of bacteria or fungi (Bouchon A et al. Nature 2001; 230:1103-7). The inventors have determined that TREM-1 is shed or secreted from the membrane of activated phagocytes and can be found in a soluble form in body fluids and is therefore a useful diagnostic marker. The presence of a soluble form of TREM-1 (sTREM-1) in bronchoalveolar lavage (BAL) fluid from mechanically ventilated patients is shown herein to be a good indicator of infectious pneumonia.

Furthermore, as described herein, the use of a plasmatic sTREM-1 assay in a group of severely ill patients admitted with signs of acute, severe inflammation can distinguish sepsis from severe systemic non-infectious inflammation Accordingly, the present invention provides methods and compositions for the clinical screening and diagnosis of disease of bacterial or fungal origin, for example, pneumonia or sepsis. In addition, the present invention provides methods and compositions for monitoring the effectiveness of the treatment of disease of bacterial or fungal origin, for example, pneumonia or sepsis, for selecting participants in clinical trials relating disease of bacterial or fungal origin, for identifying subjects most likely to respond to a particular therapeutic treatment for disease of bacterial or fungal origin and for screening and development of drugs for treatment of disease of bacterial or fungal origin.

Thus, in a first aspect the invention provides a method of diagnosis of disease of bacterial or fungal origin in a subject, which method comprises the step of measuring the level of sTREM-1 in a biological sample obtained from said subject. Generally, the disease is an inflammatory state, and said method is capable of identifying a microbial origin for said inflammatory state. Examples of such inflammatory states pneumonia and sepsis of bacterial or fungal origin.

Thus, in a first embodiment of this aspect, the invention provides a method of diagnosis of pneumonia in a subject, which method comprises the step of measuring the level of sTREM-1 in a biological sample obtained from said subject.

In a second embodiment of this aspect, the invention provides a method of diagnosing sepsis of bacterial or fungal origin in a subject, which method comprises the step of measuring the level of sTREM-1 in a biological sample obtained from said subject.

In other words, the invention provides methods of diagnosing or monitoring disease of bacterial or fungal origin, for example, pneumonia or sepsis in a patient, comprising: measuring the level of sTREM-1 in a sample from the patient, wherein the level is an indicator of presence or extent of disease of bacterial or fungal origin in the patient.

As stated above sTREM-1 is a soluble form of the TREM-1 Receptor which can be detected in certain body fluid samples by an antibody raised against the TREM-1 Receptor.

The term "pneumonia" as defined herein, means, an inflammation of the lung caused by infection by extracellular pathogens such as bacterial infection, and non-bacterial infections (for example, infection by *Blastomyces dermatitidis, Histoplasma capsulatum, Coccidioides, Sporothrix schenckii, Pneumocystis carinii, Cryptococcus, Aspergillus*, or *Mucor* sp.), protozoal infections or parasitic infections (for example, those caused by *Toxoplasma gondii, Strongyloides stercoralis, Ascaris*, hookworm, Dirofilaria, Paragonimus, or *Entamoeba histolytica*) where increased expression of sTREM-1 can be detected. Pneumonia includes "Lobar Pneumonia" (which occurs in one lobe of the lung) and Bronchopneumonia (tends to be irregularly located in the lung). Furthermore, pneumonia is often classified into two categories that may help predict the organisms that are the most likely culprits. "Community-acquired (pneumonia contracted outside the hospital). Pneumonia" in this setting often follows a viral respiratory infection. It affects nearly 4 million adults each year. It is likely to be caused by *Streptococcus pneumoniae*, the most common pneumonia-causing bacteria. Other organisms, such as atypical bacteria called *Chlamydia* or *Mycoplasma* pneumonia are also common causes of community-acquired pneumonia. "Hospital-acquired pneumonia" contracted within the hospital is often called nosocomial pneumonia. Hospital patients are particularly vulnerable to gram-negative bacteria and staphylococci.

The term "sepsis of bacterial or fungal origin" as defined herein, means, SIRS (Systemic Inflammatory Response Syndrome) associated with infection by extracellular pathogens such as bacterial infection, for example bacteremia (the presence of bacteria in the blood) with or without organ failure, and non-bacterial infections, such as fungemia (for example, yeast infection by *Candida albicans*), protozoal infections or parasitemia (such as in filariasis, malaria, and trypanosomiasis) where increased expression of sTREM-1 can be detected. Without wishing to be bound by theory, the Inventors suspect that sTREM-1 expression is not usually increased in incidences of infection and sepsis caused by intracellular pathogens such as viruses.

In this aspect, the measurement of the level of sTREM-1 comprises the steps of (a) contacting said biological sample with a compound capable of binding sTREM-1; and (b) detecting the level of sTREM-1 present in the sample by observing the level of binding between said compound and sTREM-1.

The assay or measurement of the sample for the levels of sTREM-1 present in the sample may be carried out using standard protocols known in the art. For example, where the observation of binding between sTREM-1 and the compound capable of binding sTREM-1 takes place, this observation may be carried out using known methodologies. For example the binding may be detected through use of a competitive immunoassay, a non-competitive assay system using techniques such as western blots, a radioimmunoassay, an ELISA (enzyme (inked immunosorbent assay), a "sandwich" immunoassay, an immunoprecipitation assay, a precipitin reaction, a gel diffusion precipitin reaction, an immunodiffusion assay, an agglutination assay, a complementfixation assay, an immunoradiometric assay, a fluorescent immunoassay, a protein A immunoassay, an immunoprecipitation assay, an immunohistochemical assay, a competition or sandwich ELISA, a radioimmunoassay, a Western blot assay, an immunohistological assay, an immunocytochemical assay, a dot blot assay, a fluorescence polarization assay, a scintillation proximity assay, a homogeneous time resolved fluorescence assay, a IAsys analysis, and a BIAcore analysis The determination of the incidence of disease of bacterial or fungal origin, for example, pneumonia or sepsis (depending on the state of the patient and the type of sample) can be undertaken by comparing the levels of sTREM-1 present in the sample with those in a control sample, the median level in a group of control samples (for example, samples from healthy individuals) or with data derived from previous analyses (for example provided as a standard curve or illustration with a diagnostic kit of the invention or data within a computer program, for example associated with a diagnostic means of the invention). The determination of the incidence of bacterial or fungal origin may comprise deriving the likelihood ratio using a multivariate analysis based on distribution parameters from a set of reference data derived from analysis of the levels of sTREM-1 in patients in which disease of bacterial or fungal origin is absent, present or in remission.

The invention therefore also provides diagnostic means capable of measuring levels of sTREM-1 and/or comparing said levels to known levels that are indicative of the disease state of the patient. Such diagnostic means can take the form of a stick test, for example carrying the necessary reagents to perform the method of the invention and to produce, for example, a colorimetric result which can be compared against a colour chart. Other diagnostic means which include a sample measuring means and/or a data processing means containing standard data, as mentioned above, with associated programs for comparing such data with data from a sample are also envisaged.

Thus, in the above embodiments, the method according to the first aspect of the invention can comprise the further step of c) correlating the detected level of sTREM-1 with the presence or absence of disease of bacterial or fungal origin, for example, pneumonia or sepsis. For example, a correlation can be made by comparing the measured level of sTREM-1 in the sample with a mean level in samples obtained from a control population of individuals not having disease of bacterial or fungal origin, to indicate the presence or extent of disease of bacterial or fungal origin in the patient.

In a further embodiment, the method according to the first aspect of the invention can be used in monitoring the progression or remission of disease of bacterial or fungal origin, in other words, to indicate the progression or remission of the disease. Such methods can be used to monitor the effectiveness and/or progress of therapy in a subject. In this embodiment, the method further comprises the steps of measuring the level of sTREM-1 in a second or further sample from the patient, the first and second or further samples being obtained at different times; and comparing the levels in the samples to indicate the progression or remission of the disease of bacterial or fungal origin.

The diagnostic methods according to the present invention are carried out ex vivo. Biological samples for analysis by the methods of the invention can be obtained using methods known in the art from various sources, in particular from body fluids such as whole blood, blood serum, blood plasma, urine and bronchoalveolar lavage fluid. The sample should be a sample treated such that any sTREM-1 present is not removed prior to the assay or is rendered undetectable.

Where a patient has symptoms of suspected pneumonia, a preferred biological sample is a sample of bronchoalveolar lavage fluid.

Where a patient has symptoms of SIRS, a preferred biological sample is a sample of blood serum.

The methods of the invention are applicable to mammals, for example humans, non-human primates, sheep, pigs, cows, horses, goats, dogs, cats and rodents, such as mouse and rat. Generally, the biological sample tested by the methods of the invention is a human sample. The biological sample should generally contain protein molecules from the test subject and is handled such that proteins in the sample are not rendered undetectable by the compound chosen to detect them.

In the present application, the term "compound capable of binding sTREM-1" means polypeptides, ligands, antibodies or otherwise discriminating entities which predominantly, preferably specifically, bind to sTREM-1. Such binding compounds, or "sTREM-1 binding partners" can be a naturally occurring sTREM-1 binding molecule, for example a ligand for the TREM-1 Receptor or sTREM-1 and natural and synthetic variants thereof. Further examples of binding compounds include, a chemically modified or genetically modified derivative of a sTREM-1 binding molecule, an artificially (for example chemically produced) sTREM-1 binding molecule or a recombinant or engineered soluble sTREM-1 binding molecule.

Included within the scope of the invention are antibodies which bind predominately, preferably specifically or exclusively to, sTREM-1 including, but not limited to, those antibodies which are: mono- or polyclonal antibodies (for example, raised against sTREM-1), bi-specific, multi-specific, human, humanized, chimeric antibodies, single chain antibodies, antibodies derived from phage display techniques, Fab fragments, F(ab')2 fragments, disulfide-linked Fvs, and fragments containing either a VL or VH domain or even a complementary determining region (CDR) that specifically binds to sTREM-1.

Otherwise modified immunoglobulins are also included within the scope of the invention, for example a fusion of the TREM-1-Receptor to one or more immunoglobulin-derived protein domains, for example to confer solubility and/or stability, for example human IgG or IgM Fc fragments.

In addition, substances or products mimicking the tertiary structure of a ligand for the TREM-1-Receptor can be used as binding partners specific for sTREM-1. It is possible to design such on the basis of computer modelling. The product can be produced synthetically using chemical means. Use of recombinant DNA technology to engineer the required structure is also possible as is chemical modification.

Furthermore, it is envisaged that isolated TREM-1-Receptor or sTREM-1, or computer modelling using the structure of TREM-1-Receptor or sTREM-1, may be used to produce binding partners specific for sTREM-1 using methods known in the art.

In a preferred embodiment, a compound capable of binding sTREM-1 is an antibody raised against the TREM-1 receptor, a fragment thereof or a variant thereof, provided that it is capable of binding sTREM-1. For example, such an antibody is one raised against TREM-1 human Fc (TREM-1-Fc) fusion protein (see Example 1 herein).

According to a second aspect of the invention there is provided, compounds and pharmaceutical compositions for use in the diagnosis, prognosis, treatment or monitoring of the treatment of disease of bacterial or fungal origin, for example, pneumonia or sepsis.

In one embodiment of this second aspect, the invention provides a compound capable of binding sTREM-1 for use in the diagnosis, prognosis, treatment or monitoring of disease of bacterial or fungal origin, for example, pneumonia or sepsis.

In another embodiment, the invention provides use of a compound capable of binding sTREM-1 in a method of treatment or diagnosis of disease of bacterial or fungal origin, for example, pneumonia or sepsis.

In a further embodiment, the invention provides use of a compound capable of binding sTREM-1 in the manufacture of a medicament for the diagnosis, prognosis, treatment or monitoring of the treatment disease of bacterial or fungal origin, for example, pneumonia or sepsis.

The methods described herein can furthermore be used as screening assays to identify a subject with, or at risk of developing, disease of bacterial or fungal origin, for example, pneumonia or sepsis. Such assays can be used to determine whether a subject can be administered an agent (e.g., an agonist, antagonist, peptidomimetic, protein, peptide, nucleic acid, small molecule, or other drug candidate) to treat disease of bacterial or fungal origin. For example, such methods can be used to determine whether a subject can be effectively treated with a specific agent or class of agents (e.g., antibacterial or antifungal agents). Thus, the present invention provides methods for determining whether a subject can be effectively treated with an agent for disease of bacterial or fungal origin, for example, pneumonia or sepsis in which a test sample is obtained and TREM-1 is detected.

A further embodiment of the invention provides a pharmaceutical composition comprising a compound capable of binding sTREM-1 together with a pharmaceutically acceptable diluent, carrier or excipient for use in the diagnosis or treatment of disease of bacterial or fungal origin, for example, pneumonia or sepsis.

Accordingly, also provided is the use of a compound capable of binding sTREM-1 in a method of treatment or diagnosis of disease of bacterial or fungal origin, for example, pneumonia or sepsis. In other words, the use in diagnosis and treatment of disease of bacterial or fungal origin, for example, pneumonia or sepsis, of a compound capable of binding sTREM-1. The invention also provides a compound capable of binding sTREM-1 for use in, or used in, a method of diagnosis or treatment of disease of bacterial or fungal origin, for example, pneumonia or sepsis.

As used herein the language "pharmaceutically acceptable diluent, carrier or excipient" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be included in a container, pack, or dispenser together with instructions for administration A third aspect of the invention provides a method of identifying agonists or antagonists of sTREM-1 said method comprising comparing the level of binding in a sample containing said sTREM-1 and a compound capable of binding sTREM-1, in the presence and absence of a compound to be tested. Also provided by are agonists or antagonists of sTREM-1 identified according to the method of this aspect of the invention. Also provided is a method of screening compounds for use in the therapy of disease of bacterial or fungal origin, for example, pneumonia or sepsis, comprising determining the effect of those compounds on levels of sTREM-1 present in samples brought into contact with said compounds. Accordingly, the invention also provides a method of treating disease of bacterial or fungal origin, for example, pneumonia or sepsis, in a subject, which method comprises administering to an individual in need thereof an effective amount of an inhibitor of expression or activity of sTREM-1.

In a fourth aspect, the invention provides kits, associated reagents and contacting means. In one embodiment the invention provides a kit comprising at least one compound capable of binding sTREM-1 and reagents for detecting binding of said compound to sTREM-1.

One embodiment provides a kit comprising at least one compound capable of binding sTREM-1 and means for contacting said compound with a sample containing sTREM-1.

For sTREM-1 binding compound-based kits, the kit can comprise, for example: (1) a binding compound (e.g., attached to a solid support) that binds to sTREM-1; and, optionally, (2) a second, different binding compound e.g. an antibody, which binds to either the sTREM-1 or the first binding compound and is conjugated to a detectable agent.

Such kits can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container, and all of the various containers are within a single package, along with instructions for determining whether the subject from which the sample is derived is suffering from or is at risk of developing disease of bacterial or fungal origin, for example, pneumonia or sepsis.

As discussed above "an antibody raised against the TREM-1-Receptor, a fragment thereof or a variant thereof" can function as a compound capable of binding sTREM-1. Antibodies are preferably raised against the human TREM-1-Receptor (triggering receptor expressed on myeloid cells) for which the cDNA sequence is given in [SEQ ID NO:1]. The TREM-1-Receptor is expressed on human myeloid cells, is a transmembrane protein of the immunoglobulin superfamily (Ig-SF). The TREM-1-Receptor is a transmembrane glycoprotein having the amino acid sequence of [SEQ ID NO:2] that is selectively expressed on blood neutrophils and a subset of monocytes but not on lymphocytes and other cell types.

Accordingly, the invention encompasses antibodies raised against isolated or recombinantly prepared TREM proteins or polypeptides or fragments, homologues, derivatives, or variants thereof, as defined herein, as "TREM-1-Receptor-derived polypeptides"

In accordance with the definition of "compound capable of binding sTREM-1", such antibodies raised against "TREM-1-Receptor-derived polypeptides" predominantly, preferably specifically, bind sTREM-1. Such antibodies may be tested for binding with cells expressing the TREM-1 receptor and preferably also a sample from a patient known to have been suffering from pneumonia or sepsis of bacterial or fungal origin.

The term "homologue," especially "TREM-1-Receptor homologue" as used herein refers to any member of a series of peptides to which antibodies capable of binding sTREM-1 can be raised: TREM-1-Receptor homologues can be from either the same or different species of animals.

The term "variant" as used herein refers either to a naturally occurring allelic variation of a given peptide or a recombinantly prepared variation of a given peptide or protein in which one or more amino acid residues have been modified by amino acid substitution, addition, or deletion.

The term "derivative" as used herein refers to a variation of given peptide or protein that are otherwise modified, i.e., by covalent attachment of any type of molecule, preferably having bioactivity, to the peptide or protein, including non-naturally occurring amino acids.

The human TREM-1-Receptor cDNA is 884-nucleotide long (FIG. 1; [SEQ ID NO:1]) and the open reading frame of TREM-1-Receptor is nucleotides 48 to 752 of [SEQ ID NO:1], which encodes a transmembrane protein comprising the 234 amino acid sequence shown in FIG. 2 [SEQ ID NO:2]. The human TREM-1-Receptor cDNA can be found in the GenBank database under accession number AF196329. The putative transmembrane domain starts from amino acid residues 201 to 229 of [SEQ ID NO:2] and contains a charged lysine residue at position 217. Its cytoplasmic tail consists of 5 amino acid residues and appears to contain no signaling motifs.

In a particular and preferred embodiment, antibodies for binding sTREM-1 are raised against a TREM-1-Receptorderived polypeptide comprising at least an extracellular domain comprising amino acid residues 17 to 200 of [SEQ ID NO:2].

In addition to the antibodies described above, other antibodies suitable for use in the invention are those antibodies having the ability to bind sTREM-1 which are raised against homologues of TREM-1-Receptor from either the same or different species of animal, preferably from mammals, more preferably from rodents, such as mouse and rat, and most preferably from human.

Homologues of the TREM-1-Receptor nucleic acid molecule (i.e., [SEQ ID NO:1]) can be isolated based on their close nucleotide sequence identity to the human nucleic acid molecules disclosed herein, by standard hybridization techniques under stringent or moderately stringent conditions, as defined herein below, using the human cDNA of the invention or a portion thereof as a hybridization probe.

Aspects of the invention can be also applied in the framework of multiple diagnosis of a subject. For example, in a method of screening a patient for presence or susceptibility to disease, comprising performing a plurality of diagnostic tests on a tissue sample from the patient for a plurality of diseases, the invention provides the improvement wherein one of the diagnostic tests comprises measuring the level of sTREM-1.

The various aspects and embodiments of the invention described above also apply to the following: a diagnostic means for detecting disease of bacterial or fungal origin, for example, pneumonia or sepsis; a diagnostic kit comprising such a diagnostic means; a method of treatment of infection, which includes the step of screening an individual for disease of bacterial or fungal origin, for example, pneumonia or sepsis, wherein disease of bacterial or fungal origin is correlated with the levels of sTREM-1 in a sample from said individual, and if disease of bacterial or fungal origin is identified, treating that individual to prevent or reduce the infection; and the use, in the manufacture of means for detecting disease of bacterial or fungal origin, for example, pneumonia or sepsis, of a compound capable of binding sTREM-1.

For clarity it should be noted that in the aspects and embodiments of the invention described above, the diagnosis of pneumonia alone or sepsis alone will be inferred by both the detected level of sTREM-1 and the symptoms of the patient. Generally a bronchoalveolar lavage sample from a patient with lung-related symptoms would be used to diagnose pneumonia based upon elevated levels of sTREM-1. A blood serum sample from a patient exhibiting symptoms of SIRS would be used to diagnose sepsis of bacterial or fungal origin based upon elevated levels of sTREM-1.

Thus the invention also provides a method of diagnosing disease of bacterial or fungal origin in a subject, which method comprises the step of measuring the level of sTREM-1 and the step of measuring the level of TREM-1-Ligand in one or more biological samples obtained from said subject.

As described in Example 4 herein, the Inventors have developed an immuno-enzymatic (in this case ELISA) based method for the detection of soluble TREM-1. Thus the invention provides a method of diagnosing disease of bacterial or fungal origin in a subject, which method comprises the step of measuring the level of sTREM-1 in a biological sample obtained from said subject and wherein the level of sTREM-1 is measured by an immunochemical technique. Examples of such immunochemical techniques are indirect immunofluorescence (IIF), immunoperoxydase (POD), western immunoblotting (WB), radioimmunoprecipitation (RIPA), enzyme linked immunosorbent assay (ELISA), radioimmunoassay (RIA), and agglutination assays. In a preferred embodiment an ELISA method, using an anti-human Trem-1 antibody is used to measure the level of sTREM-1.

WO2004081233 describes a method of diagnosing bacterial or fungal sepsis in a subject by measuring the level of TREM-1-Ligand in a biological sample obtained from the subject and compounds capable of binding TREM-1-Ligand. The level of TREM-1-Ligand present in the sample is measured by observing the level of binding between these compounds and TREM-1-Ligand. As described in Example 4 herein, the Inventors have determined that measurement of both soluble TREM-1 (as described herein) and membrane associated TREM-1 Ligand (as described in WO2004081233) in newly admitted critically ill patients allows the rapid identification those with infection.

Preferred features of each aspect of the invention are applicable to each other aspect, mutatis mutandis.

The present invention will now be described with reference to the following non-limiting examples, with reference to the figures, in which:

FIG. 1. shows Human TREM-1-Receptor cDNA [SEQ ID NO:1].

FIG. 2. shows Human TREM-1-Receptor amino acid sequence [SEQ ID NO:2].

FIG. 3. shows the levels of sTREM-1 in bronchoalveolar lavage fluid from patients according to diagnosis. Individual values are plotted and the bars represent the means of the values. P<0.001 between CAP and NP and between VAP and NP. NP: patients without pneumonia (n=64); CAP: Community-acquired pneumonia (n=38); VAP: Ventilator-associated pneumonia (n=46)

FIG. 4. shows receiver-operating-characteristic curves for various cut-off levels of bronchoalveolar lavage fluid sTREM-1, Tumor necrosis factor-α and Interleukin-1β in differentiating between presence and absence of pneumonia. Areas under the ROC curves for:
  sTREM-1: 0.93 (95% confidence interval, 0.92 to 0.95)
  Tumor necrosis factor-α: 0.64 (95% confidence interval, 0.62 to 0.69)
  Interleukin-1β: 0.69 (95% confidence interval, 0.67 to 0.72)

FIG. 5. shows bronchoalveolar lavage fluid (BAL) supernatants examined by Western blot analysis using 21C7, an anti TREM-1 monoclonal antibody:
  Lane 1: positive control (sTREM-1, 50 pg/mL)
  Lane 2: BAL supernatant from a patient with pneumonia
  Lane 3: BAL supernatant from a patient without pneumonia FIG. 6. shows a flow-chart of the patients admitted to the ICU during the study period.

FIG. 7. shows admission plasmatic levels of C-Reactive Protein, Procalcitonin and sTREM-1 according to diagnosis. Individual values are plotted and the bars represent the means of the values. P<0.001 between SIRS and Sepsis and between SIRS and Septic Shock:
  SIRS: patients with systemic inflammatory response syndrome of non-infectious origin (n=29)
  Sepsis: patients with sepsis or severe sepsis (n=22)
  Septic Shock: patients with septic shock (n=25)

FIG. 8. shows Receiver-operating-characteristic curves for various cut-off levels of plasmatic C-Reactive Protein, Procalcitonin and sTREM-1 in differentiating between presence and absence of infection. Areas under the ROC curves for:
  C-Reactive Protein: 0.77 (95% confidence interval, 0.69 to 0.85)
  Procalcitonin: 0.85 (95% confidence interval, 0.81 to 0.89)
  sTREM-1: 0.97 (95% confidence interval, 0.94 to 1.0)

FIG. 9. shows admission plasmatic levels of C-Reactive Protein, Procalcitonin and sTREM-1 in patients with sepsis, severe sepsis and septic shock according to outcome. Individual values are plotted and the bars represent the means of the values. P Values are 0.26, 0.64 and 0.05 between Survivors and Non-Survivors for C-Reactive Protein, Procalcitonin and sTREM-1 respectively.

FIG. 11 shows the kinetics of immuno-enzymatic assay to detect soluble TREM-1 (panel A) and the cytofluorimetric analysis of TREM-1 Ligand (panel B) in a patient having SIRS without infection (HSR34) and in a sepsis patient (HSR37).

Figure 14:
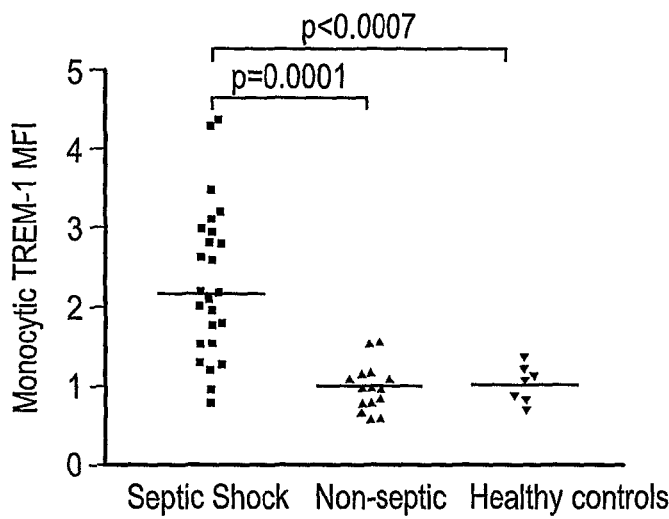

FIG. 14 shows analysis of cell surface expression of TREM-1 in monocytes from septic patients (n=25) and non-septic patients (n=15) or healthy controls (n=7). Results were expressed as Mean Fluorescence Intensity (MFI). Respective p values (Student's t test) are depicted above each scatter plot.

Figure 15:
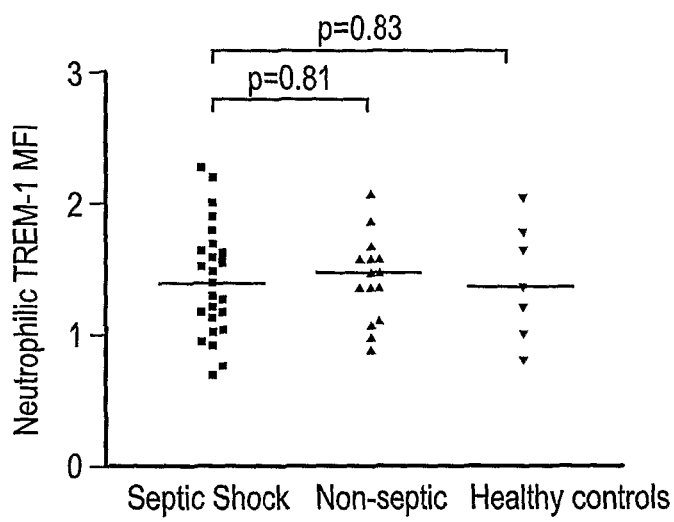

FIG. 15 shows analysis of cell surface expression of TREM-1 in polymorphonuclear cells from septic patients (n=25) and non-septic patients (n=15) or healthy controls (n=7). Results were expressed as Mean Fluorescence Intensity (MFI). Respective p values (Student's t test) are depicted above each scatter plot.

Figure 16:
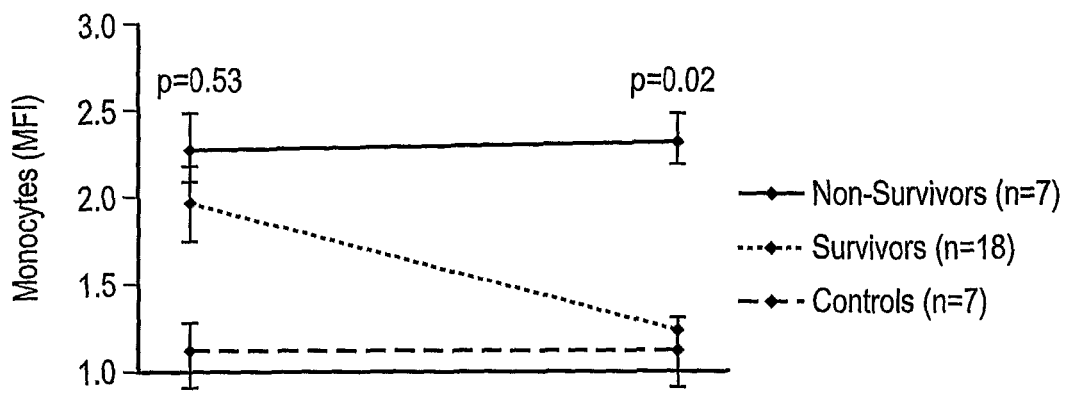

FIG. 16 shows TREM-1 expression pattern on monocytes during septic shock according to outcome. Results are expressed as Mean Fluorescence Intensity. Respective p values are depicted above time points. 'Baseline' corresponds to the first determination and 'Last value' to the last determination of TREM-1 before intensive care unit discharge or death.

EXAMPLES

Example 1

Production of Antibodies Against TREM-1 Receptor which are Capable of Binding sTREM-1

Antibodies were raised against a fusion protein of the TREM-1 receptor with the human IgG Fc region. To produce soluble TREM-1-Fc, the cDNA fragment encoding the TREM-1 extracellular region was amplified by PCR and cloned into an expression vector containing the exons for hinge, CH2, and CH3 region of human IgG1 (see Bouchon of al. The Journal of Immunology, 2000, 164: 4991-4995). Briefly, the 760-bp TREM-1 was amplified by RT-PCR, cloned into pCR2.1 (Invitrogen, Carlsbad, Calif.), and sequenced. The PCR primers used were:

5'-GCTGGTGCACAGGAAGGATG [SEQ ID NO: 3]
3'-GGCTGGAAGTCAGAGGACATT [SEQ ID NO: 4]

This chimeric gene was transfected into mouse myeloma cell line J558L, screening of culture supernatants, and purification of TREM-1-Fc can then be performed, as previously described (Traunecker, et al., 1991, *Trends Biotechnol.* 9:109)).

Anti-TREM-1 monoclonal antibodies (mAbs) were produced by immunising BALB/c mice with TREM-1-Fc. Briefly, 10-wk-old, female BALB/c mice (Iffa-Credo, L'Arbresle, France) received an initial injection of 100 pg of TREM-1-Fc fusion protein (TREM-1-Fc), mixed 1:1 (vol/vol) with Alu-Gel-S (Serva Biochemicals, Paramus, N.J.), behind the neck. Four weeks later, they were given a booster immunization with the same immunogen, followed after 2 weeks by a final injection of 100 pg of purified TREM-1-Fc. Three days later, mice were sacrificed and draining lymph node cells were isolated and fused with the myeloma fusion partner, Ag8.653, using polyethylene glycol 4000. Hybridoma supernatants were screened in two steps. First, an ELISA was performed using TREM-1-Fc in the coating step and human-adsorbed alkaline phosphatase-labeled goat anti-mouse IgG as secondary antibody. Supernatants from clones that were positive in ELISA were then tested by FACS® analysis for staining cells by flow cytometry.

Example 2

Rapid Detection of the Soluble Form of TREM-1 (sTREM) in the Diagnosis of Pneumonia Materials and Methods
Study Population Approval of the institutional review board and informed consent from patients or their relatives were obtained before inclusion. All patients 18 years or older hospitalized in the Inventors' medical ICU were prospectively enrolled in the study if they met the following criteria: 1) need for mechanical ventilation; 2) clinical suspicion of infectious pneumonia defined by a newly developed and persistent infiltrate on chest radiography associated with at least one of the following: purulent tracheal secretions, body temperature of at least 38.3° C., and leukocytosis (>10000/mm$^3$) or leukopenia (<4000/mm$^3$). Ventilator-associated pneumonia was defined by acquisition of the disease after 48 h of mechanical ventilation. On admission into the ICU, the following items were recorded for each patient: age; sex; severity of underlying medical condition stratified according to the criteria of McCabe and Jackson (McCabe W R, Jackson G G. Arch Intern Med 1982; 110:847-64); SAPS II score; Sepsis-related Organ Failure Assessment (SOFA) score (range, 0 to 24, with scores for each organ system [respiration, coagulation, liver, cardiovascular, central nervous system, and kidney] ranging from 0 [normal] to 4 [most abnormal]); and reason for admission into the ICU. The following baseline variables were also recorded at inclusion: SAPS II score; SOFA score; body temperature; leukocyte count; ratio of the partial pressure of arterial oxygen to the fraction of inspired oxygen (PaO$_2$/FiO$_2$); serum levels of C reactive protein and procalcitonin; presence of shock, defined as systolic arterial pressure lower than 90 mm Hg with signs of peripheral hypoperfusion or need for continuous infusion of vasopressor or inotropic agents; duration of previous mechanical ventilation; and use of previous antimicrobial therapy. A clinical pulmonary infection score (CPIS) was calculated as previously described in Pugin J, et al. Am Rev Respir Dis 1991; 143:1121-9. The duration of mechanical ventilation, length of ICU stay and ICU mortality were also recorded.

Confirmation of the Diagnosis

Mini-bronchoalveolar lavages (BAL) and microbiological specimen processing were performed as described in detail in Papazian L et al. Am J Respir Crit Care Med 1995; 152:1982-91 and Duflo F et al. Anesthesiology 2002; 1:74-9. Briefly, mini-bronchoalveolar lavage was performed using the Combicath, a single-sheathed, 50-cm, sterile, plugged, telescopic catheter (Plastimed, St Leu La Forêt, France). The recovered BAL fluid (13±3 mL out of 20 mL of instilled saline serum) was divided into two samples: one was used for direct microscopic examination and quantitative culture; the other was centrifuged at 10000 revolutions per minute for 30 min and the supernatant was frozen at −80° C. until used for sTREM-1 and cytokine measurements. The concentration of microorganisms considered significant for the potential diagnosis of pneumonia was >$10^3$ cfu/mL of BAL fluid. Post hoc diagnosis of pneumonia was made from a combination of already mentioned clinical criteria with microbiological evidence of microbial infection. These criteria were similar to those used for ventilator-associated pneumonia described in Pugin J et al. Am Rev Respir Dis 1991; 143:1121-9.

Pneumonia was considered to be absent when an alternative cause for pulmonary infiltrate was established and there was non-significant bacterial growth in culture of BAL in association with full recovery from fever, infiltrate, and leukocytosis without antimicrobial therapy. Two intensivists reviewed all medical records pertaining to the patient and independently classified the diagnosis as community-acquired pneumonia, ventilator-associated pneumonia or no pneumonia. A consensus concerning the diagnosis was achieved in all cases. Both intensivists were blinded to the results of sTREM-1 and cytokines levels.

sTREM-1 and Cytokines Assays

Assessment of sTREM-1 levels in BAL fluid samples was performed using an immunoblot technique with 21C7, a monoclonal murine IgG1 directed against human TREM-1 prepared as described in Example 1. Briefly, 100 μL of each BAL fluid supernatant was dotted on a nitrocellulose membrane, dried, and overcoated in phosphate buffer-saline (PBS) supplemented with 3% bovine serum albumin. The nitrocellulose sheet was then incubated for 60 min in the presence of diluted 1:2000 diluted 21C7. After thorough rinsing, the sheet was further incubated for 60 min with diluted 1:1000 diluted goat anti-mouse immunoglobulins (Dako, Glostrup, Denmark), washed in PBS supplemented with 20% dimethylsulfoxyde and incubated for 30 min with diluted 1:1000 diluted horseradish peroxydase-conjugated streptavidin (Bio-Rad, Cergy, France). The enzyme substrate chromogen Opti-4CN (Bio-Rad) was then added, and colour developed in proportion to the amount of sTREM-1 bound to the membrane. Each sheet also contained calibration samples of a known concentration of sTREM-1 (0 to 200 pg/mL). Colorimetric determination was achieved by means of a reflectance scanner and the Quantity One Quantitation Software (Bio-Rad). sTREM-1 concentration from each sample was determined by comparing the optical densities of the samples to the standard curve. All measurements were performed in duplicate and results are expressed as the mean concentration in picograms per milliliter of bronchoalveolar lavage fluid. The sensitivity of this technique allows the detection of sTREM-1 level as low as 5 pg/mL and the entire procedure takes less than 3 hours. The coefficient of variation of the assay was lower than 5 percent. Tumor necrosis factor-α and interleukin-1β were determined in BAL fluid by solid-phase ELISA method according to the recommendations of the manufacturer (BD Biosciences, Le Pont de Claix, France). The sensitivity of the technique allows the detection of levels as low as 2 pg/mL for tumor necrosis factor-α and 3.9 pg/mL for interleukin-1β.

Statistical Analysis

Descriptive results of continuous variables were expressed as mean (±SD). The results of BAL sTREM-1 and cytokines levels were expressed as mean (±SD). Variables were tested for their association with diagnosis using Pearson $\chi^2$ test for categorial data and Mann-Whitney U test for numerical data. Comparison between the different groups was conducted by using Mann-Whitney U test (or non-parametric Kruskall-Wallis test when appropriate) for numerical data and using Pearson $\chi^2$ test for categorial data. The relations between sTREM-1 and clinical or biological features were assessed using Spearman's correlation test. To evaluate the value of the presence of sTREM-1 in BAL fluid, the Inventors used a multiple stepwise logistic regression model with the use of P value 0.05 or less for entry into the model. The predictors included clinical and laboratory findings along with information on the presence of sTREM-1 in BAL fluid. Receiver-operating-characteristic (ROC) curves were constructed to illustrate various cut-off values of sTREM-1, tumor necrosis factor-α and interleukin-1β. Analysis was completed with Statview software (Abacus Concepts, Berkeley Calif.) and a two-tailed P<0.05 was considered significant.

Results

Characteristics of the Patients 1097 patients were admitted into the ICU. All the 148 patients fulfilling the inclusion criteria were enrolled. The baseline characteristics of the overall study group are shown in table 2.

TABLE 2

Characteristics of the studied population.

| Characteristic | All patients (n = 148) | Community-acquired pneumonia (n = 38) | Ventilator-associated pneumonia (n = 46) | No pneumonia (n = 64) | P value |
|---|---|---|---|---|---|
| Age, years (±SD) | 60 ± 15 | 58 ± 17 | 59 ± 14 | 62 ± 14 | 0.53 |
| Sex, n (%) | 95 (64) | 24 (63) | 29 (63) | 42 (66) | |
| Male | 53 (36) | 14 (37) | 17 (37) | 22 (34) | 0.97 |
| Female | | | | | |
| McCabe score, mean (±SD) | 1.85 ± 0.95 | 1.77 ± 0.92 | 1.81 ± 0.92 | 1.88 ± 0.91 | 0.79 |
| History of COPD*, n (%) | 39 (26) | 9 (23) | 12 (26) | 18 (28) | 0.93 |
| SAPS II score†, mean (±SD) | 52 ± 17 | 53 ± 20 | 50 ± 15 | 53 ± 17 | 0.76 |
| SOFA score§*, mean (±SD) | 7.8 ± 3.9 | 8.5 ± 4.4 | 7.0 ± 3.5 | 8.1 ± 4.0 | 0.43 |

TABLE 2-continued

Characteristics of the studied population.

| Characteristic | All patients (n = 148) | Community-acquired pneumonia (n = 38) | Ventilator-associated pneumonia (n = 46) | No pneumonia (n = 64) | P value |
|---|---|---|---|---|---|
| Reason for admission n (%) Acute respiratory failure | 42 (28.3) | 23 (61) | 4 (9) | 15 (24) | 0.002 |
| Neurologic | 41 (27.7) | 7 (18) | 15 (33) | 19 (30) | 0.45 |
| Shock | 37 (25) | 6 (16) | 16 (35) | 15 (23) | 0.18 |
| Miscellaneous | 28 (19) | 2 (5) | 11 (24) | 15 (23) | 0.08 |
| Length of mechanical ventilation, days (±SD) | 14 ± 12 | 8 ± 7 | 21 ± 19 | 11 ± 9 | <0.001 |
| Length of ICU stay, days (±SD) | 18 ± 15 | 11 ± 8 | 26 ± 21 | 15 ± 9 | <0.001 |
| Mortality, n (%) | 50 (34) | 11 (29) | 19 (41) | 20 (31) | 0.58 |

*COPD: chronic obstructive pulmonary disease
†SAPS II: Simplified Acute Physiologic Score II
§SOFA: Sepsis-related Organ failure Assessment
P values are comparisons between CAP, VAP and NP groups Most of the patients had an associated co-morbidity and 38 (26 percent) had a history of chronic obstructive pulmonary disease (COPD). Mean (±SD) SAPSII and SOFA scores were 52 (±17) and 7.8 (±3.9) respectively. The ICU mortality rate of 34 percent was in agreement with the predictive risk of death based on the SAPSII score (Le Gall J R et al., JAMA 1993; 270:2957-63). Diagnosis was established as community-acquired pneumonia (CAP) in 38 patients (26 percent), ventilator-associated pneumonia (VAP) in 46 patients (31 percent) and no pneumonia (NP) in 64 patients (43 percent). Among the NP group, diagnoses were established as follows: Acute exacerbation of COPD (n=11); Acute respiratory distress syndrome (ARDS) of extra-pulmonary origin (abdominal or uro-genital sepsis: n=19; pancreatitis: n=6; others: n=4); ARDS of pulmonary origin (near-drowning: n=1; fire smoke inhalation: n=1); Cardiogenic shock (n=12) and Unknown (n=10). Clinical characteristics of the three groups did not differ significantly at inclusion (table 1). Community-acquired pneumonia patients were more often referred to the ICU with acute respiratory failure than others (P=0.002). As expected, the duration of mechanical ventilation and length of ICU stay were higher among ventilator-associated pneumonia patients (P<0.001). Mortality did not differ between the three groups. A clinical pulmonary infection score (CPIS)>6 was more frequent in community-acquired and ventilator-associated pneumonia patients than in no-pneumonia patients (P=0.02). Body temperature, leukocyte count, ratio of the partial pressure of arterial oxygen to the fraction of inspired oxygen ($PaO_2/FiO_2$), serum C reactive protein (CRP) and procalcitonin levels did not differ between the three groups (Table 3).

Microbial species grew at a significant concentration from BAL (>$10^3$ CFU/mL) of all except 2 community-acquired pneumonia patients infected with *Legionella pneumophila* and of all ventilator-associated pneumonia patients as shown in Table 4.

TABLE 3

Characteristics of the 3 groups of patients at inclusion.

| Characteristic | Community-acquired pneumonia (n = 38) | Ventilator-associated pneumonia (n = 46) | No pneumonia (n = 64) | P value |
|---|---|---|---|---|
| Duration of mechanical ventilation before study entry, days (±SD) | 0.4 ± 0.2 | 6.4 ± 8.5 | 2.1 ± 4.8 | <0.001 |
| Previous antimicrobial therapy, n (%) | 33 (87) | 19 (41) | 30 (47) | <0.001 |
| Shock, n (%) | 18 (47) | 19 (41) | 30 (47) | 0.49 |
| Body temperature, °C. (±SD) | 37.9 ± 2.0 | 38.1 ± 0.9 | 37.7 ± 1.1 | 0.82 |
| Leukocyte count, cells/mm³ (±SD) | 12800 ± 7900 | 13400 ± 8500 | 12500 ± 5800 | 0.99 |
| $PaO_2/FiO_2$*, mmHg (±SD) | 181 ± 80 | 203 ± 67 | 206 ± 91 | 0.51 |
| CPIS† > 6, n (%) | 23 (60) | 28 (61) | 22 (34) | 0.02 |
| Procalcitonin, ng/mL (±SD) | 3.7 ± 1.9 | 2.6 ± 0.8 | 2.5 ± 1.2 | 0.58 |
| C reactive protein, mg/L (±SD) | 197 ± 128 | 184 ± 108 | 141 ± 110 | 0.34 |
| BAL§ fluid TNFα, pg/mL (±SD) | 298.2 ± 47.7 | 290.5 ± 39.7 | 147.2 ± 25.1 | <0.001 |
| BAL§ fluid IL-1β, pg/mL (±SD) | 92.5 ± 22.5 | 95.1 ± 29.4 | 41.5 ± 12.5 | <0.001 |

TABLE 3-continued

Characteristics of the 3 groups of patients at inclusion.

| Characteristic | Community-acquired pneumonia (n = 38) | Ventilator-associated pneumonia (n = 46) | No pneumonia (n = 64) | P value |
|---|---|---|---|---|
| BAL§ fluid sTREM-1, pg/mL (±SD) | 23.2 ± 2.8 | 33.6 ± 5.1 | 1.8 ± 0.9 | <0.001 |

*PaO$_2$/FiO$_2$: ratio of the partial pressure of arterial oxygen to the fraction of inspired oxygen
†CPIS: clinical pulmonary infection score
§BAL: bronchoalveolar lavage
P values are comparisons between CAP, VAP and NP groups

TABLE 4

Features and organisms associated with pneumonia

| Feature or Organism | Community-acquired pneumonia (n = 38) | Ventilator-associated pneumonia (n = 46) |
|---|---|---|
| Monomicrobial pneumonia, n (%) | 36 (95) | 37 (80) |
| Polymicrobial pneumonia, n (%) | 2 (5) | 9 (20) |
| Total number of pathogens*, n | 40 | 58 |
| Bacilli, n (%) | | |
| Pseudomonas aeruginosa | | 12 (20.7) |
| Haemophilus influenzae | 10 (25) | 10 (17.2) |
| Acinetobacter baumanii | | 4 (6.9) |
| Serratia marcescens | | 6 (10.3) |
| Klebsiella species | 1 (2.5) | 6 (10.3) |
| Legionella pneumophilia | 3 (7.5) | |
| Miscellaneous | 2 (5) | 2 (3.4) |
| Cocci, n (%) | | |
| Staphylococcus aureus | 4 (10) | 14 (24.1) |
| Streptococcus species | 1 (2.5) | |
| Streptococcus pneumonia | 17 (42.5) | 1 (1.7) |
| Fungi | 2 (5) | 3 (5.2) |

*Organisms shown are those that were isolated at significant concentrations from quantitative cultures of bronchoalveolar lavage fluid (>10$^3$ colony-forming units/mL). Legionnella pneumophilia infection was diagnosed by the detection the soluble urinary antigen.

sTREM-1, Tumor Necrosis Factor-α and Interleukin-1β Levels

Figure 3:
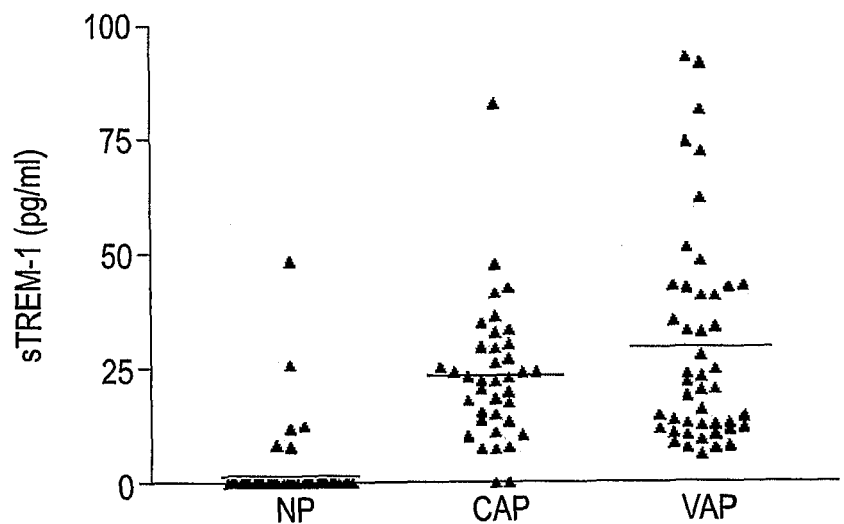

The levels of sTREM-1 were higher in BAL fluid from community-acquired and ventilator-associated pneumonia patients than from no-pneumonia patients (P<0.001) but did not differ significantly between community-acquired and ventilator-associated pneumonia patients (FIG. 3). Tumor necrosis factor-α and interleukin-1β levels showed the same trend (P<0.001) but with a large overlap of values. Among patients with pneumonia, there was a trend (P=0.07) towards higher sTREM-1 levels in non-survivors than in survivors with 31.2±5.7 pg/mL and 24.9±3.0 pg/mL respectively. There was no correlation between sTREM-1 levels and previous history of chronic obstructive pulmonary disease, amount of inflammatory cells in BAL fluid, microbial species or any other clinical and biological features.

Diagnostic Value of sTREM-1 Assay

Figure 4:
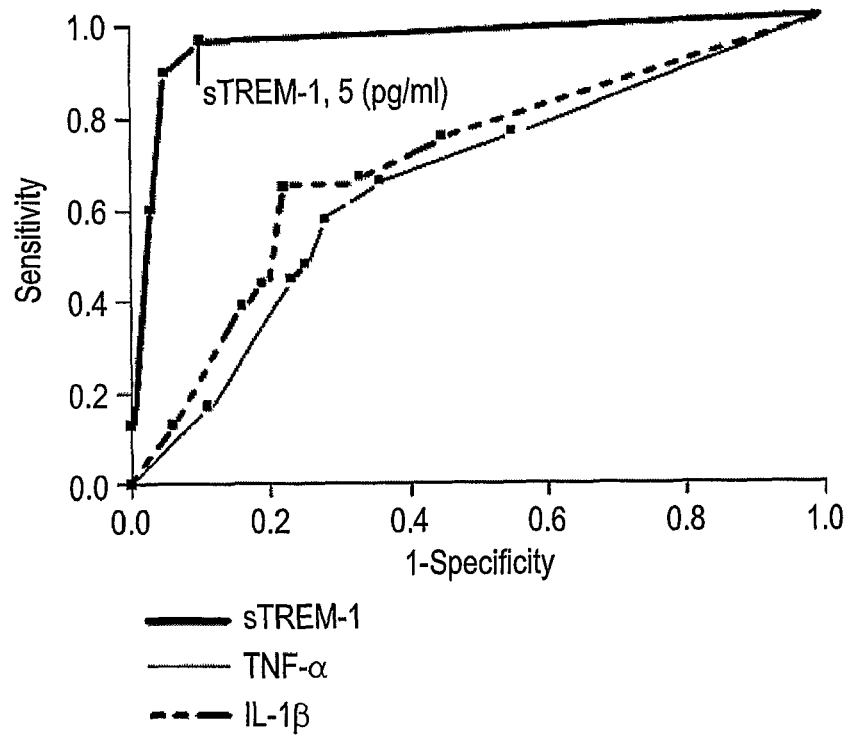
Figure 5:
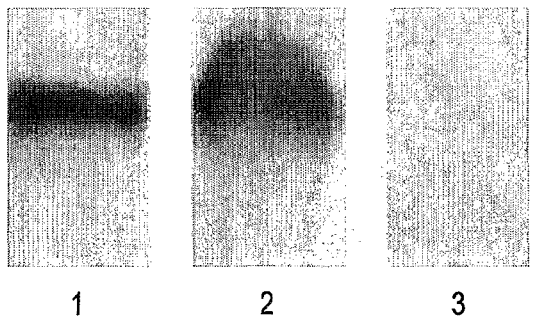
Figure 6:
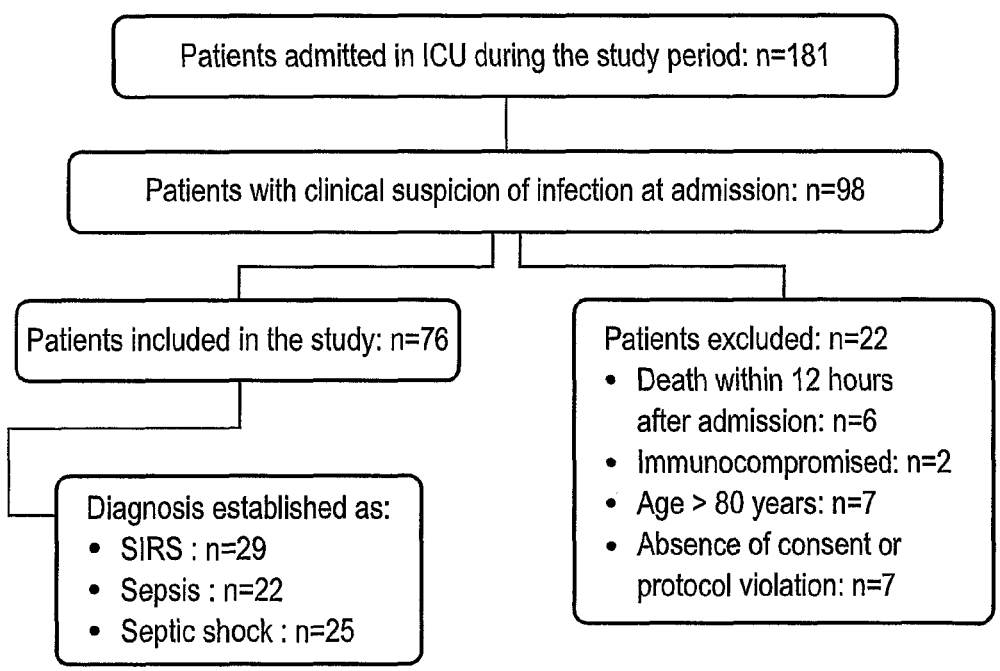

The Inventors next determined whether the presence of sTREM-1 in bronchoalveolar lavage fluid could discriminate between presence and absence of pneumonia. Since there was no difference between community-acquired and ventilator-associated pneumonia patients for the following analyses, pooled data are presented. Whatever the level at or above 5 pg/mL, sTREM-1 was detected in BAL fluid among 36 out of 38 community-acquired pneumonia patients (sensitivity: 95 percent, 2 false negatives), 46 out of 46 ventilator-associated pneumonia patients (sensitivity: 100 percent), and in 6 out of 64 no-pneumonia patients (6 false positives). Thus, among the whole population of patients, the presence of sTREM-1 in BAL fluid is associated with a likelihood ratio of 10.38. The capacity of sTREM-1 to differentiate pneumonia from no pneumonia was assessed with a ROC curve analysis (FIG. 4). The area under the ROC curve when sTREM-1 was used to differentiate pneumonia from no pneumonia was 0.93 (95 percent CI 0.92 to 0.95, P<0.001). A sTREM-1 cut-off value of 5 pg/mL (which represented the technique's threshold of detection) had a sensitivity of 98 percent (95 percent CI, 95 to 100) a specificity of 90 percent (95 percent CI, 84 to 96). In a multiple logistic regression analysis, the Inventors determined that the presence of sTREM-1 in BAL fluid was the strongest independent predictor of pneumonia with an odds ratio of 41.52 (table 5). The best clinical predictor of pneumonia was a clinical pulmonary infection score >6 (odds ratio: 2.98).

TABLE 5

Multiple logistic-regression analysis of factors used for differentiating between patients with and those without pneumonia

| PREDICTOR | P Value | ODDS RATIO (95% Confidence Interval) |
|---|---|---|
| CPIS* > 6 | 0.002 | 2.98 (1.51 to 5.86) |
| BAL TNFα > 150 pg/mL | 0.004 | 2.44 (1.82 to 5.75) |
| BAL IL-1β > 75 pg/mL | 0.003 | 2.70 (1.97 to 13.18) |
| BAL sTREM-1 > 5 pg/mL | <0.001 | 41.52 (20.90 to 77.62) |

*CPIS: clinical pulmonary infection score

These results demonstrate that rapid detection of the sTREM-1 in bronchoalveolar lavage fluid improves the ability of clinicians to differentiate patients with bacterial or fungal pneumonia from those without pneumonia. This should be especially useful among patients in whom the diagnosis is not clinically straightforward. The immunoblot technique is rapid, accurate, of very low cost and can be applied to small series or even individual samples. Use of this test to detect the presence of sTREM-1 in bronchoalveolar lavage fluid will lead to more accurate diagnoses of pneumonia in mechanically ventilated patients. Microbiological documentation was obtained in all cases of community-acquired and ventilator-associated pneumonia. When pneumonia was considered to be absent, either a non-infectious alternative cause for pulmonary infiltrate was established or patients fully recovered from fever, infiltrate, and leukocytosis without antimicrobial therapy. However, the Inventors could not exclude that some patients with a true ventilator-associated pneumonia could have been misclassified in the no-pneumonia group and spontaneously recovered. This could have artificially lowered the specificity of the test and may have been responsible for some of the 6 false-positives in the no-pneumonia group. Finally, and without wishing to be bound by theory, none of the patients tested presented with a viral pneumonia and thus, results are not generalisabie to viral infections.

Example 3

Diagnostic Value of Plasmatic Levels of the Soluble Form of Triggering Receptor Expressed on Myeloid Cells (TREM)-1 in Critically Ill Patients with Suspected Sepsis Materials and Methods
Study Population All consecutive patients newly hospitalized in a teaching hospital medical ICU in France were prospectively enrolled in the study if they had a clinically suspected infection and fulfilled at least two criteria of SIRS (Bone R C, at al. Chest. 1992; 101:1644-55.). Clinically suspected infection was defined as an explicit statement by the attending physician indicating the suspicion of an ongoing infection, combined with the initiation of a diagnostic work-up to identify or rule out infection and the prescription of antimicrobial therapy. Patients were not enrolled if they were older than 80 years of age or were immunocompromised (treatment with corticosteroids, bone marrow or organ transplant recipients, leukopenia [white blood cells count <1 G/L] or neutropenia [polymorphonuclear granulocyte count <0.5 G/L], hematologic malignancy or acquired immune deficiency syndrome). Patients who presented with early death or discharge (within 12 hours after admission) or complete absence of antimicrobial treatment were also excluded. Patients originated either from the emergency room, the general wards, or from the operating room. Approval of the institutional review board and informed consent from patients or their relatives were obtained before inclusion.

Data Collection

Upon admission into the ICU, the following items were recorded for each patient: age; sex; severity of underlying medical condition stratified according to the criteria of McCabe and Jackson (Arch Intern Med. 1982; 110:847-64); Simplified Acute Physiology Score II (SAPSII) (Le Gall J R et al. JAMA. 1993; 270:2957-63); Sepsis-related Organ Failure Assessment (SOFA) score (range 0 to 24, with scores for each organ system [respiration, coagulation, liver, cardiovascular, central nervous system, and kidney] ranging from 0 [normal] to 4 [most abnormal]) (Vincent J L et al. Intensive Care Med. 1996; 22:707-10); reason for admission into the ICU; principal diagnosis; vital signs; respiratory parameters; routine blood tests and microbiologic culture results. Survival or death in the ICU was assessed during a follow-up period as long as 28 days. Microbiologic tests and antimicrobial therapy were prescribed by the attending physician according to the usual practice of the ICU without interference by the research team. Two intensivists retrospectively reviewed all medical records pertaining to each patient and independently classified the diagnosis as SIRS, sepsis, severe sepsis, or septic shock at the time of admission, according to established consensus definitions (Bone R C, et al. Chest. 1992; 101:1644-55.). Agreement concerning the diagnosis was achieved in all cases. Both intensivists were blinded to the results of plasmatic sTREM-1 values.

Measurements of Procalcitonin and sTREM-1 Plasma Levels

Within 12 hours after admission and enrolment in the study, 5 mL of whole heparinized blood was drawn via an arterial line for PCT and sTREM-1 determinations. Plasma was collected by centrifugation at 4° C., aliquoted, and stored at −80° C. until the day of assay. Plasmatic PCT concentrations were measured using an immunoassay with a sandwich technique and a chemiluminescent detection system, according to the manufacturer's protocol (LumiTest; Brahms Diagnostica, Berlin, Germany). Assessment of plasmatic sTREM-1 levels was performed as described in Example 2. Briefly, 100 µL of each plasma sample was dotted on a nitrocellulose membrane, dried, and overcoated in phosphate buffer-saline (PBS) supplemented with 3% bovine serum albumin. The nitrocellulose sheet was then incubated for 60 min in the presence of monoclonal anti-TREM-1 antibody 21C7, a murine IgG1 directed against human TREM-1, prepared as described in Example 1.

After thorough rinsing, the sheet was further incubated for 60 min with 1:1000 diluted goat anti-mouse immunoglobulins (Dako, Glostrup, Denmark), washed in PBS supplemented with 20% dimethylsulfoxide and incubated for 30 min with 1:1000 diluted horseradish peroxydase-conjugated streptavidin (Bio-Rad, Cergy, France). The enzyme substrate chromogen Opti-4CN (Bio-Rad) was then added, and colour developed in proportion to the amount of sTREM-1 bound to the membrane. Each sheet also contained calibration samples of a known concentration of sTREM-1 (0 to 5000 ng/mL). Colorimetric determination was achieved by means of a reflectance scanner and the Quantity One Quantitation Software (Bio-Rad). sTREM-1 concentration from each sample Was determined by plotting the optical densities of the samples to the standard curve. All measurements were performed in duplicate and results expressed as mean concentration in nanograms per mL of plasma. The sensitivity of this technique allows the detection of sTREM-1 levels as low as 5 ng/mL and the entire procedure takes less than 3 hours. The coefficient of variation of the assay was lower than 5 percent.

Statistical Analysis

Descriptive results of continuous variables were expressed as mean (±SD). The results of plasmatic sTREM-1 and PCT levels were expressed as mean (±SD). Variables were tested for their association with the diagnosis using Pearson $\chi^2$ test for categorial data and Mann-Whitney U test for numerical data. Comparison between the different groups was conducted by using Mann-Whitney U test (or non-parametric Kruskal-Wallis test when appropriate) for numerical data and using Pearson $\chi^2$ test for categorial data. The relations between sTREM-1 and clinical or biological features were assessed using Spearman's correlation test. To evaluate the value of the sTREM-1 plasmatic levels assay, the inventors used a multiple stepwise logistic regression model. The predictors included clinical and laboratory findings along with information on plasmatic sTREM-1 level. For the purpose of logistic regression analysis, which requires binary outcome events, subjects classified as confirmed sepsis, severe sepsis, or septic shock (sepsis syndrome) were compared to patients with SIRS and initial suspicion of infection. Receiver-operating-characteristic (ROC) curves were constructed to illustrate various cut-off values of sTREM-1, PCT and CRP. Sensitivity, specificity, and positive and negative predictive values of each parameter were calculated according to standard methods. These values were calculated for the cut-off that represented the best discrimination as derived from the areas under ROC curves. Analysis was completed with Statview software (Abacus Concepts, Berkeley Calif.) and a two-tailed $P<0.05$ was considered significant.

Results
Characteristics of the Study Population 98 patients were admitted into an ICU with clinical suspicion of infection, of whom 22 were not included in the study because of early death, immunocompromised state, age over 80 years old, absence of consent or protocol violation (FIG.

6). The baseline characteristics of the overall study group are shown in table 6. Mean (±SD) SAPSII and SOFA scores were 50.5 (±22.6) and 8.3 (±4.5) respectively. The ICU mortality rate of 26.3% was in agreement with the predictive risk of death based on the SAPSII score. Diagnosis was established as SIRS in 29 patients (38%), sepsis or severe sepsis (grouped as 'Sepsis') in 22 patients (29%) and septic shock in 25 patients (33%). Causative conditions of SIRS were as follow: cardiac surgery (n=6); cardiogenic shock (n=5); acute exacerbation of chronic obstructive pulmonary disease (n=5); acute pancreatitis (n=3); heat stroke (n=3); gastro-intestinal haemorrhage (n=2); trauma (n=1) and unknown (n=4). Clinical characteristics did not differ significantly at inclusion between septic and non-septic patients (Table 6). Infections were microbiologically proven in 40 of 49 infected patients (82%) with 55% Gram-negative, 42% Gram-positive bacteria, and 3% fungal infections. The major sources of infection were the respiratory tract (55%) and abdomen (22%). Twenty-four percent of infected patients had a documented bloodstream infection. Neither site of infection nor microbial strains differed between surviving and non-surviving patients (Table 7).

TABLE 6

Clinical and biological data at admission and outcome of the patients.

| Characteristic* | Total (n = 76) | Septic patients (n = 47) | Non-septic patients (n = 29) | P value |
|---|---|---|---|---|
| Age, years | 60 (15) | 61 (14) | 59 (15) | 0.55 |
| Sex† | | | | |
| Male | 54 (71) | 37 (79) | 17 (59) | 0.06 |
| Female | 22 (29) | 10 (21) | 12 (41) | |
| McCabe | 1.3 (0.8) | 1.3 (0.8) | 1.3 (0.9) | 0.57 |
| Simplified Acute Physiology Score II | 50.5 (22.6) | 52.6 (23.8) | 46.5 (20.5) | 0.65 |
| SOFA score | 8.3 (4.5) | 9.7 (4.8) | 5.8 (2.6) | 0.38 |
| Temperature, °C. | 37.9 (1.0) | 37.9 (1.1) | 37.9 (1.0) | 0.38 |
| Leukocytes, G/L | 14.4 (7.6) | 14.4 (8.2) | 13.9 (3.8) | 0.61 |
| C-Reactive Protein, mg/L | 154.1 (142.8) | 203.9 (147.7) | 62.7 (65.3) | 0.002 |
| Procalcitonin, ng/mL | 20.9 (44.3) | 31.4 (52.4) | 1.1 (2.2) | <0.001 |
| sTREM-1, ng/mL | 1121 (953) | 1611 (826) | 229 (341) | <0.001 |
| Length of ICU stay, days | 6.4 (7.9) | 6.4 (5.3) | 6.3 (11.5) | 0.37 |
| Mortality rate† | 20 (26.3) | 15 (31.9) | 5 (17.2) | 0.16 |

*Values are expressed as mean (SD) unless otherwise indicated. P values are for the comparison of Septic vs Non-septic patients.
†Values are expressed as number (percentage)

TABLE 7

Septic patients: Sites of infection and strains diagnosed at the onset of sepsis according to outcome.

| | Total (n = 49) | Survivors (n = 34) | Non-Survivors (n = 15) | P value* |
|---|---|---|---|---|
| Patients who had positive microbial documentation of infection | 40 (82) | 28 (82) | 12 (80) | 0.96 |
| Patients who had positive blood culture result | 12 (24) | 7 (21) | 5 (33) | 0.54 |
| Site of infection | | | | |
| Lung | 27 (55) | 18 (53) | 9 (60) | 0.67 |
| Abdominal | 11 (22) | 6 (18) | 5 (33) | 0.53 |
| Genito-urinary | 5 (11) | 5 (15) | 0 (0) | 0.26 |
| Cellulitis | 3 (6) | 2 (6) | 1 (7) | 0.97 |

TABLE 7-continued

Septic patients: Sites of infection and strains diagnosed at the onset of sepsis according to outcome.

| | Total (n = 49) | Survivors (n = 34) | Non-Survivors (n = 15) | P value* |
|---|---|---|---|---|
| Others | 3 (6) | 3 (8) | 0 (0) | 0.22 |
| Micro-organisms | N = 40 | N = 28 | N = 12 | |
| Gram-positive | 17 (42) | 12 (43) | 5 (42) | 0.61 |
| Gram-negative | 22 (55) | 16 (57) | 6 (50) | 0.64 |
| Fungi | 1 (3) | 0 (0) | 1 (8) | 0.21 |

*P values are for comparison between Survivors vs Non-Survivors

Baseline Plasmatic Levels of CRP, PCT and sTREM-1

Figure 7:
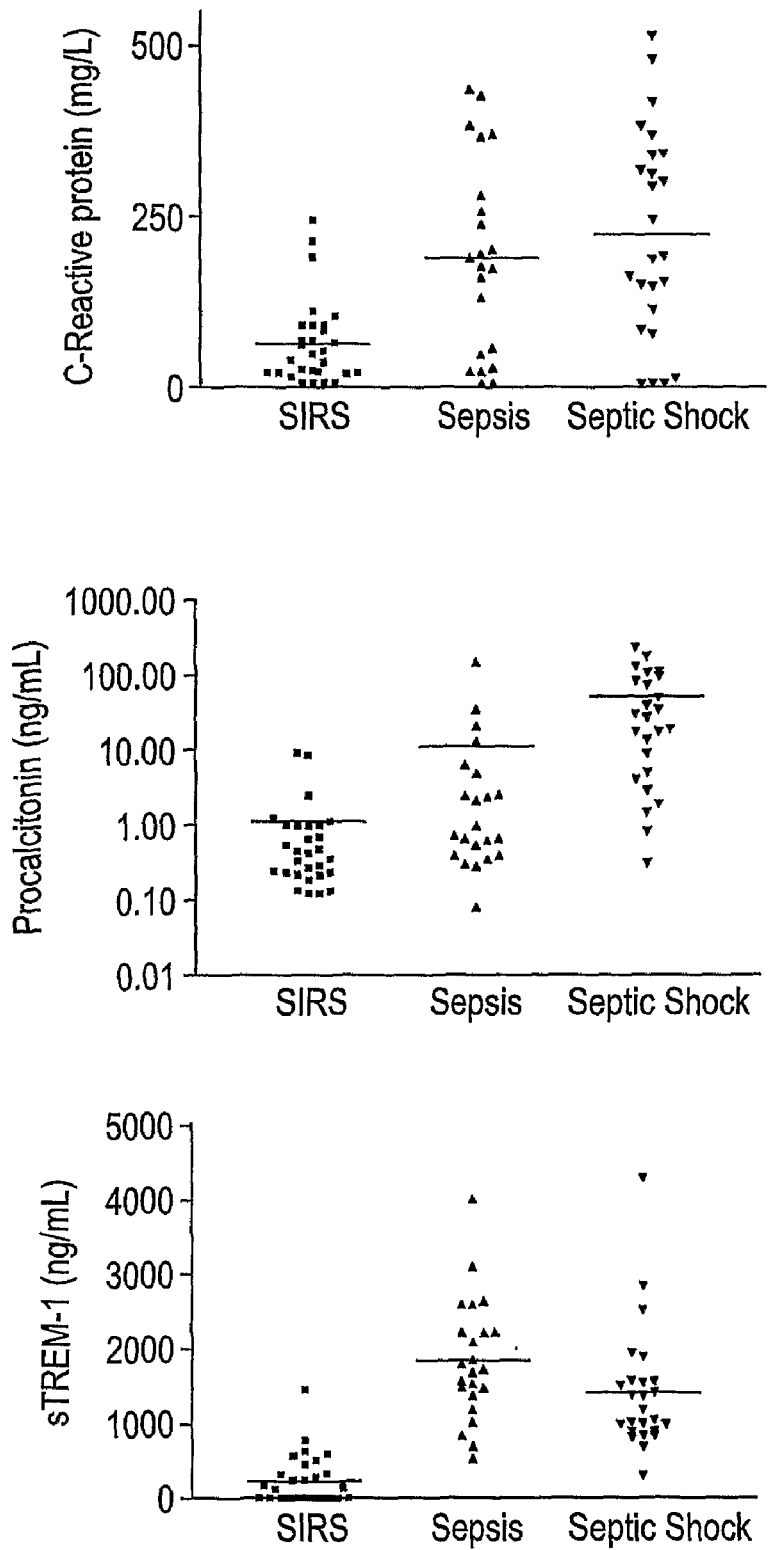
Figure 8:
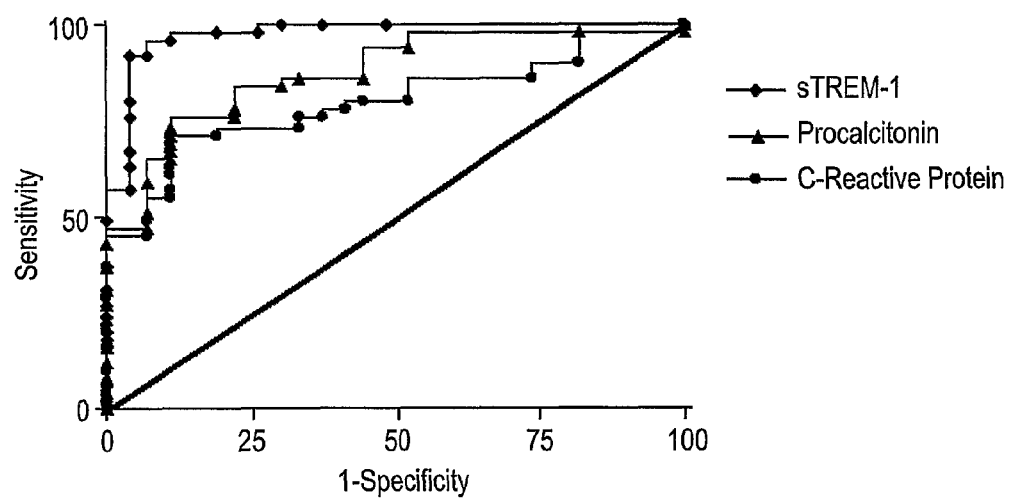

Baseline plasmatic levels of CRP, PCT and sTREM-1 were higher among septic patients than among subjects with SIRS only (Table 6, FIG. 7). Plasmatic sTREM-1 levels appeared to be most helpful in differentiating patients with sepsis from those with SIRS. Mean plasmatic sTREM-1 levels on admission were 229 ng/mL for SIRS; 1836 ng/mL for sepsis and 1413 ng/mL for septic shock (P<0.001). The accuracy of the candidate parameters to distinguish patients with SIRS from those with septic conditions was highly variable (Table 8). As shown in FIG. 8, plasmatic sTREM-1 levels yielded the highest discriminative value with an area under the ROC curve (AUC) of 0.97 (95% confidence interval [CI], 0.94 to 1.0) followed by PCT (AUC, 0.85; CI, 0.81 to 0.89) and CRP (AUC, 0.77; CI, 0.69 to 0.85; p<0.001). At a cut-off of 600 ng/mL, sTREM-1 yielded a sensitivity of 96% (95% CI, 0.92 to 100%) and a specificity of 89% (CI, 82 to 95%) to differentiate patients with SIRS from those with sepsis or septic shock. There was no correlation between sTREM-1 levels and CRP or PCT levels, microbial species or any other clinical and biological features.

TABLE 8

Diagnostic performance of different sepsis predictors.

| Cut-off value* | sTREM-1 600 ng/mL | Procalcitonin 0.6 ng/mL | C-Reactive Protein 70 mg/L |
|---|---|---|---|
| Sensitivity, % | 96 | 84 | 76 |
| Specificity, % | 89 | 70 | 67 |
| Positive predictive value, % | 94 | 84 | 80 |
| Negative predictive value, % | 92 | 70 | 60 |
| Likelihood ratio | 8.6 | 2.8 | 2.2 |
| Area under the receiver operating curve (95% confidence interval) | 0.97 (0.94-1.00) | 0.85 (0.81-0.89) | 0.77 (0.69-0.85) |

*Sensitivity, Specificity and Predictive values were calculated for the cut-off, which represented the best discrimination as derived from the receiver operating characteristic curves.

Clinical Significance of Plasmatic sTREM-1 Level

In order to investigate the diagnostic performance of plasmatic sTREM-1 levels from a clinical perspective, the Inventors conducted a multiple stepwise analysis including CRP, PCT and sTREM-1 levels. Plasmatic sTREM-1 level was found to be the strongest independent predictor of infection with an adjusted odds ratio (AOR) of 9.58 (95% CI, 2.31 to 38.90, P=0.002) (Table 9).

TABLE 9

Multivariate logistic regression analyses*.

| Variable | Regression Coefficient | SE | Odds Ratio (95% Confidence Interval) | P Value |
|---|---|---|---|---|
| Intercept | −6.25 | 2.13 | NA | 0.003 |
| C-Reactive Protein, mg/L | 0.17 | 0.09 | 1.46 (0.79-2.69) | 0.23 |
| Procalcitonin, ng/mL | 0.24 | 0.19 | 3.83 (1.00-14.66) | 0.05 |
| sTREM-1, ng/mL | 0.52 | 0.16 | 9.58 (2.31-38.90) | 0.002 |

*Results of stepwise selection procedures. Other variables entered in the model were Simplified Acute Physiology Score II, Sepsis-related Organ Failure Assessment score, White Blood Cells count and Body temperature.
NA indicates not applicable.

Severity of Sepsis and Outcome

Figure 9:
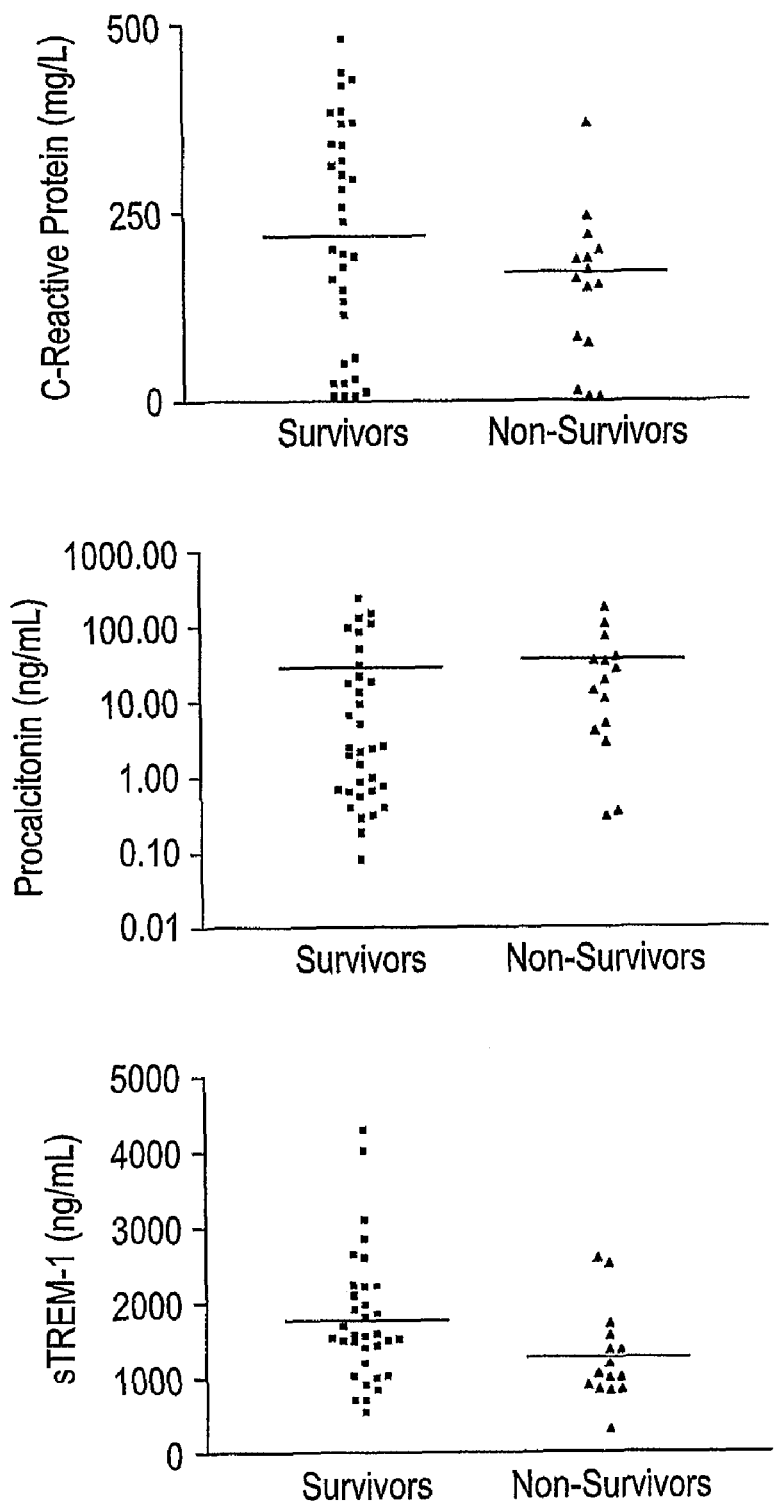
Figure 10:
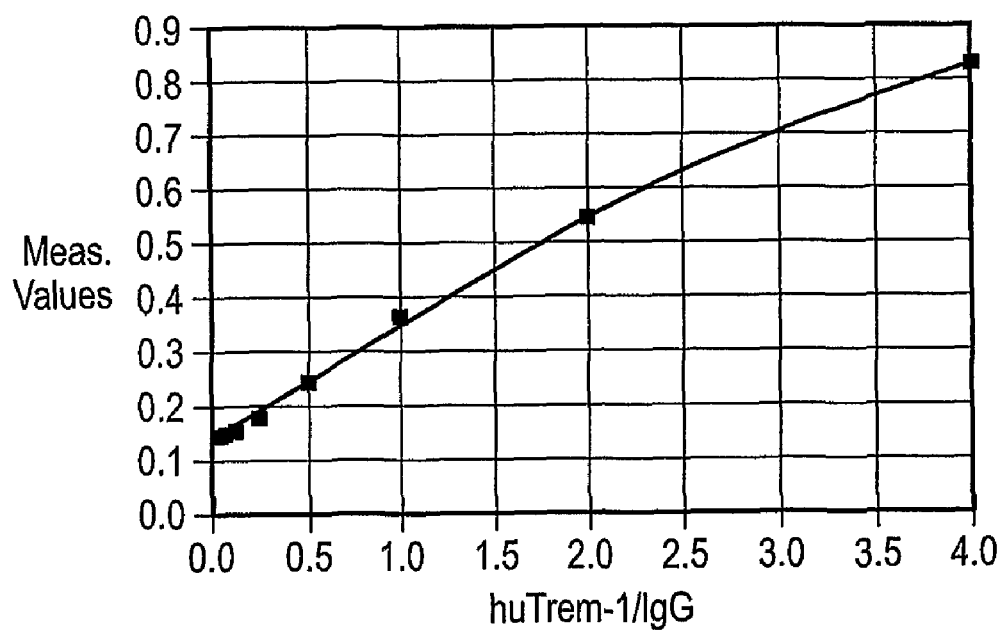
FIG. 10 shows a standard curve for an immuno-enzymatic assay to detect soluble TREM-1 in the sera of patients with suspected sepsis

The Inventors further evaluated plasmatic sTREM-1 levels in relation to the patient's prognosis. Values of plasmatic CRP, PCT and sTREM-1 levels in infected patients at the time of admission, in relation to outcome, are shown in FIG. 9. The most discriminative parameter to predict death among infected patients at the time of admission was a plasmatic sTREM-1 level below 1500 ng/mL (odds ratio, 6.6; 95 percent CI 4.5 to 20.0, P=0.03). The Inventors' study has several strengths. The study population was large and comprised a diverse group of critically ill adult patients admitted to a medical ICU in various phases of infectious and non-infectious conditions, which allowed a generalization of the study findings. The diagnosis was determined by blinded investigators without knowledge of the plasmatic sTREM-1 levels and the patients were classified as having SIRS of non-infectious origin after incorporation of all other available clinical and laboratory data (Bone R C, et al. Chest. 1992; 101:1644-55.). Finally, the Inventors' study was designed as a real-life study, not including control patients without suspected infection but only patients with a high pre-test probability of sepsis, covering the spectrum of patients that is likely to be encountered in the future use of this test.

Example 4

Use of an Immuno-Enzymatic Assay to Detect Soluble TREM-1 in the Sera of Patients with Suspected Sepsis An ELISA based method for the detection of soluble human TREM-1 with applications in the diagnosis of bacterial or fungal infection, in particular sepsis, has been developed by the Inventors.
In one example, the method is as follows:
Materials:
Plate: Nunc Maxisorp 96 well
Coating buffer: carbonate pH 9.6: 0.015 M $Na_2CO_3$ (0.794 g in 500 ml $H_2O$), 0.035 M $NaHCO_3$ (1.47 g in 500 ml $H_2O$)
Wash buffer: 0.1% Tween 20 in PBS, pH 7.4
Assay buffer: PBS+0.2% BSA
Blocking solution: PBS+3% BSA
Substrate solution: 30 mM potassium citrate, pH 4.1, immediately before use, add 1 tablet of 3,3',5,5'-Tetramethylbenzidine (Sigma # T-3405) for 10 ml of buffer and add 2.5 µl of $H_2O_2$ 30%.
Method:
a) Coating: 100 µl/well of anti-human Trem-1 Antibody (Polyclonal R&D Systems Inc, Minneapolis, Minn., USA #AF1278) (1:1000), [$C_{mother}$]: 100 µg/ml-[$C_{final}$]: 100 ng/ml) diluted in coating buffer pH 9.6.
b) Seal plate and incubate overnight at +4° C.
c) Wash 3 times with wash buffer
d) Block plates by adding 200 µl of blocking solution
e) Incubate at 37° C. for 1 hour or 2 hours at RT
f) Discard supernatant and plate 100 µl standards and samples dilute in assay buffer
g) Seal plate and incubate overnight at +4° C. or 2 hours at 37° C.
h) Wash 6 times with wash buffer
i) Add 100 µl of anti-human Trem-1 antibody (clone 21C7) diluted in assay buffer, 1:1000 [$C_{mother}$]: 1 mg/ml-[$C_{final}$] 1 µg/ml
j) incubate 2 hours at RT
k) Wash 6 times with wash buffer
l) Acid 100 µl of goat anti-mouse IgG HRP (Pierce #31430) diluted 1:5000 in assay buffer,
m) Seal plate and incubate 2 hours at RT
n) Wash 6 times with wash buffer
o) Add 100 µl of substrate solution to each well.
p) Incubate at room temperature
q) Stop the reaction with 1M $H_2SO_4$ 50 µl/well
r) Determine the optical density of each well using a microtiter reader at 450 nm
Results
The results for samples from two patients within an on-going study assayed using the method described above are shown in Table 10:

TABLE 10

| SERUM HSR34 (ng/ml) | |
|---|---|
| 34/0 | 0.3364 |
| 34/1 | 0.8662 |
| 34/2 | 1.4172 |
| 34/3 | 1.5655 |
| 34/4 | 1.7139 |
| 34/5 | 0.8662 |
| 34/6 | 0.6543 |
| 34/7 | 0.5907 |
| SERUM HSR37 (ng/ml) | |
| 37/0 | 3.9602 |
| 37/1 | 26.063 |
| 37/2 | 26.296 |
| 37/3 | 14.132 |
| 37/4 | 6.1853 |
| 37/5 | 2.5191 |
| 37/6 | 2.0741 |
| 37/7 | ND |

Patients with suspected sepsis were analyzed at different time points (/0, /7). Time 0 represents the day of admission into the Intensive Care Unit. Samples were obtained every 48 hours until day 15.
This example demonstrates that in the patients with sepsis (HSR37) soluble TREM-1 was detected at low levels (3.96 ng/ml) at the time of admission into the ICU and reached its maximal level between T2 (day 4) and T3 (day 6) (26 ng/ml). Soluble TREM-1 was not detected in the patients with SIRS with no associated sepsis. Levels of membrane associated TREM-1 Ligand (the detection of which is described in WO2004081233) were not detectable in the patient with sepsis (HSR37) at the time of admission into the ICU and reached maximal expression at T4 (day 8). These results indicate that both soluble TREM-1 and membrane associated TREM-1 Ligand are associated with the sepsis status and their expression correlates with the clinical course of the disease. Measurement of both soluble TREM-1 and membrane associated TREM-1 Ligand in newly admitted critically ill patients could help to rapidly identify those with infection.

Example 5 sTREM-1 Assay in Plasma from Septic Patients

Figure 12:
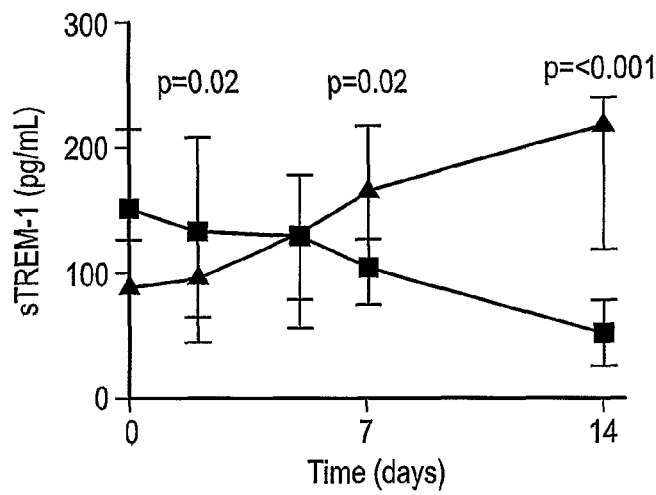
FIG. 12 shows the time course of median (with interquartile range) plasma levels of sTREM-1 in surviving (squares) and non-surviving (triangles) patients in a series of 63 patients, some with sepsis (n=30) others with septic shock (n=33).
Figure 13:
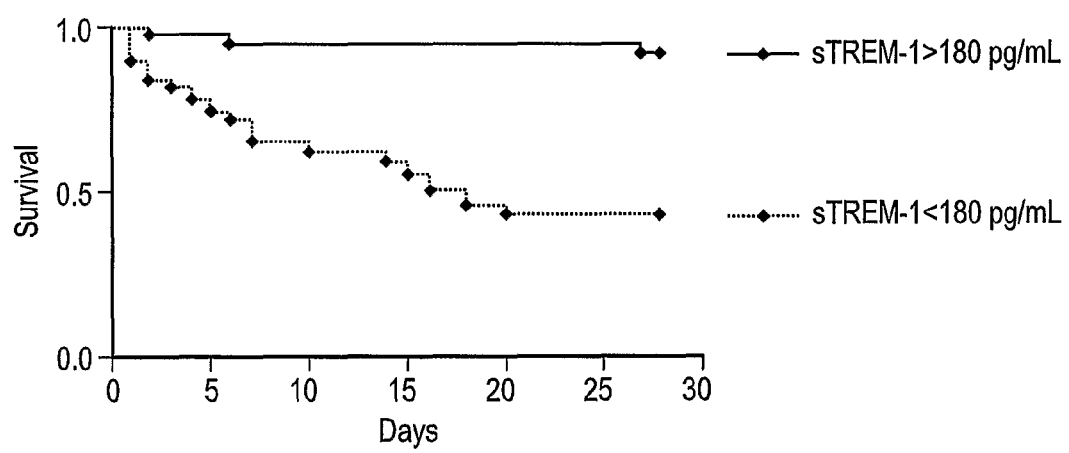
FIG. 13 shows Kaplan-Meier analysis of patients with sTREM-1>180 pg/mL (n=32) and <180 pg/mL (n=31). There was a significant difference between the two curves (Log-Rank test, p<0.01).

In another series of 63 patients, some with sepsis (n=30) others with septic shock (n=33), plasma levels of sTREM-1 were assayed. FIG. 12 shows the time course of median (with interquartile range) plasma levels of sTREM-1 in surviving (squares) and non-surviving (triangles) patients. FIG. 13 shows Kaplan-Meier analysis of patients with sTREM-1>180 pg/mL (n=32) and <180 pg/mL (n=31) at the time of admission into the ICU. There was a significant difference between the two curves (Log-Rank test, p<0.01), thus underscoring the value of assaying the soluble form of TREM-1 in plasma samples of critically ill septic patients as a useful method for assessing the evolution of the disease.

Example 6

TREM-1 Expression on PMNs and Monocytes

In further series of patients, monocyte (see FIG. 14) and polymorphonuclear (see FIG. 15) cell surface expression of TREM-1 was analysed in flow cytometry after labeling with a mouse monoclonal antibody anti-human TREM-1, PE-labelled (clone 193015, R&D, Abingdon, UK). Results were expressed as Mean Fluorescence Intensity (MFI). Three groups of patients were studied, septic patients (n=25) and non-septic patients (n=15) or healthy controls (n=7). Respective p values (Student's t test) are depicted above each scatter plot. No significant difference for the expression of membrane TREM-1 expression on neutrophils from patients of the three groups was observed. MFI on monocytes from patients with septic shock are significantly higher than MFI from non-septic patients or healthy controls.

FIG. 16 shows TREM-1 expression pattern on monocytes during septic shock according to outcome. Results are expressed as Mean Fluorescence Intensity. Respective p values are depicted above time points. 'Baseline' corresponds to the first determination and 'Last value' to the last determination of TREM-1 before intensive care unit discharge or death. These results demonstate that among patients with sepsis, those with lower levels of TREM-1 expression on monocytes, but not on neutrophils, can be predicted to have a positive outcome.

The invention claimed is:

1. A method of diagnosing disease of bacterial or fungal origin in a subject, wherein said disease is pneumonia or sepsis, which method comprises the steps of (a) measuring a level of the soluble form of the human TREM-1 receptor in a biological sample obtained from said subject;

(b) comparing the measured level of the soluble form of the human TREM-1 receptor in the sample with a mean level in a control population of individuals not having disease of bacterial or fungal origin;

(c) correlating elevated levels of the soluble form of the human TREM-1 receptor with the presence or extent of said disease of bacterial or fungal origin.

2. The method of claim 1 wherein said step of measuring the level of the soluble form of the human TREM-1 receptor comprises the steps of:
   (a) contacting said biological sample with a compound capable of binding the soluble form of the human TREM-1 receptor;
   (b) detecting the level of the soluble form of the human TREM-1 receptor present in the sample by observing the level of binding between said compound and the soluble form of the human TREM-1 receptor.

3. The method of claim 1, further comprising the steps of measuring the level of the soluble form of the human TREM-1 receptor in a second or further sample from said subject, the first and second or further samples being obtained at different times; and comparing the levels in the samples to indicate the progression or remission of the disease of bacterial or fungal origin.

4. The method of claim 1, wherein the sample is selected from the group consisting of whole blood, blood serum, blood, plasma, urine and bronchoalveolar lavage fluid.

5. The method of claim 1, wherein the sample is from bronchoalveolar lavage fluid.

6. The method of claim 1, wherein the sample is from blood serum or blood plasma.

7. The method of claim 1, wherein the sample is a human sample.

8. The method of claim 2 wherein said compound specifically binds the soluble form of the human TREM-1 receptor.

9. The method of claim 2 wherein said compound capable of binding the soluble form of the human TREM-1 receptor is an antibody raised against all or part of the TREM-1 receptor.

10. The method of claim 1, wherein the level of soluble form of the human TREM-1 receptor is measured by an immunochemical technique.

11. The method of claim 1 comprising the additional step of measuring the level of TREM-1-Ligand in one or more biological samples obtained from said subject.

* * * * *

SEQUENCE LISTING

<160> NUMBER OF SEQ ID NOS: 4

<210> SEQ ID NO 1
<211> LENGTH: 884
<212> TYPE: DNA
<213> ORGANISM: Homo sapiens

<400> SEQUENCE: 1

```
ctactactac taaattcgcg gccggtcgac gctggtgcac aggaaggatg aggaagacca      60
ggctctgggg gctgctgtgg atgctctttg tctcagaact ccgagctgca actaaattaa     120
ctgaggaaaa gtatgaactg aaagagtggc agaccctgga tgtgaaatgt gactacacgc     180
tagagaagtt tgccagcagc cagaaagctt ggcagataat aagggacgga gagatgccca     240 agacctggc atgcacagag aggccttcaa agaattccca tccagtccaa gtggggagga     300
tcatactaga agactaccat gatcatggtt tactgcgcgt ccgaatggtc aaccttcaag     360
tggaagattc tggactgtat cagtgtgtga tctaccagcc tcccaaggag cctcacatgc     420
tgttcgatcg catccgcttg gtggtgacca agggtttttc agggacccct ggctccaatg     480
agaattctac ccagaatgtg tataagattc ctcctaccac cactaaggcc ttgtgcccac     540
tctataccag ccccagaact gtgacccaag ctccacccaa gtcaactgcc gatgtctcca     600
ctcctgactc tgaaatcaac cttacaaatg tgacagatat catcagggtt ccggtgttca     660
acattgtcat tctcctggct ggtggattcc tgagtaagag cctggtcttc tctgtcctgt     720
ttgctgtcac gctgaggtca tttgtaccct aggcccacga acccacgaga atgtcctctg     780
acttccagcc acatccatct ggcagttgtg ccaagggagg agggaggagg taaaaggcag     840
ggagttaata acatgaatta aatctgtaat caccagctat ttct                      884
```

<210> SEQ ID NO 2
<211> LENGTH: 234
<212> TYPE: PRT
<213> ORGANISM: Homo sapiens

<400> SEQUENCE: 2

Met Arg Lys Thr Arg Leu Trp Gly Leu Leu Trp Met Leu Phe Val Ser

```
                    1               5                  10                  15
               Glu Leu Arg Ala Ala Thr Lys Leu Thr Glu Glu Lys Tyr Glu Leu Lys
                                20                  25                  30

Glu Gly Gln Thr Leu Asp Val Lys Cys Asp Tyr Thr Leu Glu Lys Phe
                                35                  40                  45

Ala Ser Ser Gln Lys Ala Trp Gln Ile Ile Arg Asp Gly Glu Met Pro
                                50                  55                  60

Lys Thr Leu Ala Cys Thr Glu Arg Pro Ser Lys Asn Ser His Pro Val
                65                  70                  75                  80

Gln Val Gly Arg Ile Ile Leu Glu Asp Tyr His Asp His Gly Leu Leu
                                85                  90                  95

Arg Val Arg Met Val Asn Leu Gln Val Glu Asp Ser Gly Leu Tyr Gln
                                100                 105                 110

Cys Val Ile Tyr Gln Pro Pro Lys Glu Pro His Met Leu Phe Asp Arg
                                115                 120                 125

Ile Arg Leu Val Val Thr Lys Gly Phe Ser Gly Thr Pro Gly Ser Asn
                                130                 135                 140

Glu Asn Ser Thr Gln Asn Val Tyr Lys Ile Pro Pro Thr Thr Thr Lys
               145                 150                 155                 160

Ala Leu Cys Pro Leu Tyr Thr Ser Pro Arg Thr Val Thr Gln Ala Pro
                                165                 170                 175

Pro Lys Ser Thr Ala Asp Val Ser Thr Pro Asp Ser Glu Ile Asn Leu
                                180                 185                 190

Thr Asn Val Thr Asp Ile Ile Arg Val Pro Val Phe Asn Ile Val Ile
                                195                 200                 205

Leu Leu Ala Gly Gly Phe Leu Ser Lys Ser Leu Val Phe Ser Val Leu
                                210                 215                 220

Phe Ala Val Thr Leu Arg Ser Phe Val Pro
               225                 230

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctggtgcac aggaaggatg                                                   20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggctggaagt cagaggacat t                                                 21
```